(12) United States Patent
Kusleika et al.

(10) Patent No.: US 7,578,830 B2
(45) Date of Patent: Aug. 25, 2009

(54) MINIMALLY INVASIVE MEDICAL DEVICE DEPLOYMENT AND RETRIEVAL SYSTEM

(76) Inventors: Richard S. Kusleika, 18188 Ullmann Cir., Eden Prairie, MN (US) 55346; Duy Nguyen, 14869 Overlook Dr., Savage, MN (US) 55378; Kent D. Anderson, 11205 Virginia Ave. North, Champlin, MN (US) 55316

( * ) Notice: Subject to any disclaimer, the term of this patent is extended or adjusted under 35 U.S.C. 154(b) by 988 days.

(21) Appl. No.: 10/989,787

(22) Filed: Nov. 16, 2004

(65) Prior Publication Data
US 2005/0090857 A1   Apr. 28, 2005

Related U.S. Application Data

(63) Continuation of application No. 10/184,327, filed on Jun. 27, 2002, now abandoned, which is a continuation of application No. 09/936,248, filed as application No. PCT/US00/06212 on Mar. 8, 2000, now abandoned.

(60) Provisional application No. 60/124,156, filed on Mar. 8, 1999.

(51) Int. Cl.
*A61M 29/00* (2006.01)
(52) U.S. Cl. ...................... 606/194; 606/200
(58) Field of Classification Search ................ 606/194, 606/195, 198; 623/1.11
See application file for complete search history.

(56) References Cited

U.S. PATENT DOCUMENTS

| | | | |
|---|---|---|---|
| 4,425,908 A | 1/1984 | Simon | |
| 4,619,246 A | 10/1986 | Molgaard-Nielsen et al. | |
| 4,832,055 A | 5/1989 | Palestrant | |
| 4,873,978 A | 10/1989 | Ginsburg | |
| 5,011,488 A | 4/1991 | Ginsburg | |
| 5,102,415 A | 4/1992 | Guenther et al. | |
| 5,556,389 A | 9/1996 | Liprie | |
| 5,662,671 A | 9/1997 | Barbut et al. | |
| 5,814,064 A | 9/1998 | Daniel et al. | |
| 5,827,324 A | 10/1998 | Cassell et al. | |
| 6,001,118 A | 12/1999 | Daniel et al. | |
| 6,152,946 A | 11/2000 | Broome et al. | |
| 6,171,327 B1 | 1/2001 | Daniel et al. | |

(Continued)

FOREIGN PATENT DOCUMENTS

DE    28 21 048 B1    11/1979

(Continued)

*Primary Examiner*—Vy Q Bui
(74) *Attorney, Agent, or Firm*—Popovich, Wiles & O'Connell, P.A.

(57) ABSTRACT

The present invention provides a medical device retrieval system comprising a working element carried by a flexible, elongate shaft, the working element having a proximal profile and the shaft extending proximally from the working element and a retrieval cover slidable carried along the shaft of the medical device, the cover having a deployed configuration and being capable of being compressed into a compressed configuration for deployment, yet resiliently substantially return to the deployed configuration; the cover in its deployed configuration having a radially reduced proximal portion, a distally open distal end defining a distal opening having a maximum dimension at least as great as the maximum dimension of the proximal profile of the working element of the medical device, and an elongate internal recess defined between the proximal portion and the distal end.

13 Claims, 14 Drawing Sheets

U.S. PATENT DOCUMENTS

| | | |
|---|---|---|
| 6,221,006 B1 * | 4/2001 | Dubrul et al. ............... 600/159 |
| 6,245,089 B1 | 6/2001 | Daniel et al. |
| 6,458,151 B1 | 10/2002 | Saltiel |
| 2001/0012951 A1 | 8/2001 | Bates et al. |
| 2001/0044632 A1 | 11/2001 | Daniel et al. |
| 2002/0123765 A1 | 9/2002 | Sepetka et al. |
| 2003/0040704 A1 | 2/2003 | Dorros et al. |

FOREIGN PATENT DOCUMENTS

| | | |
|---|---|---|
| WO | WO 91/11209 | 8/1991 |
| WO | WO 96/01591 | 1/1996 |
| WO | WO 97/17021 | 5/1997 |
| WO | WO 01/12082 A1 | 2/2001 |
| WO | WO 01/45592 A1 | 6/2001 |
| WO | WO 02/11627 A2 | 2/2002 |
| WO | WO 02/060519 A1 | 8/2002 |
| WO | WO 03/002035 A2 | 1/2003 |

* cited by examiner

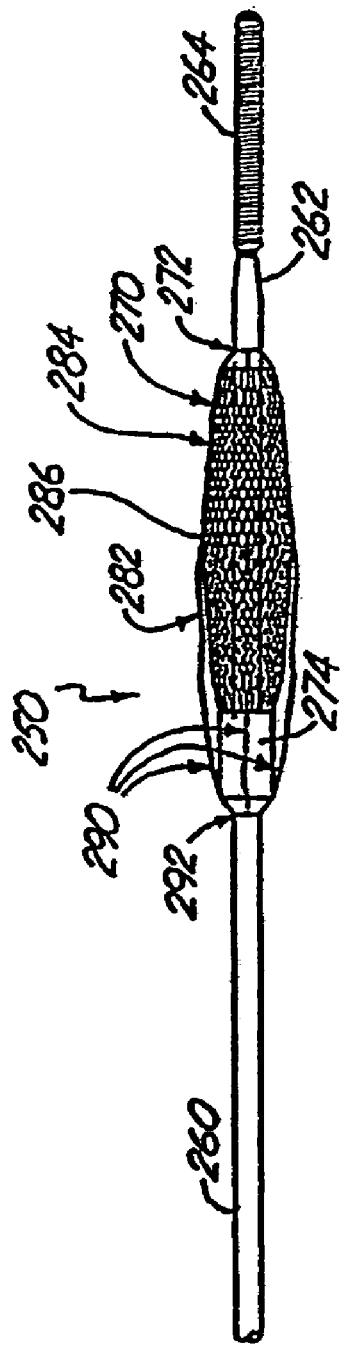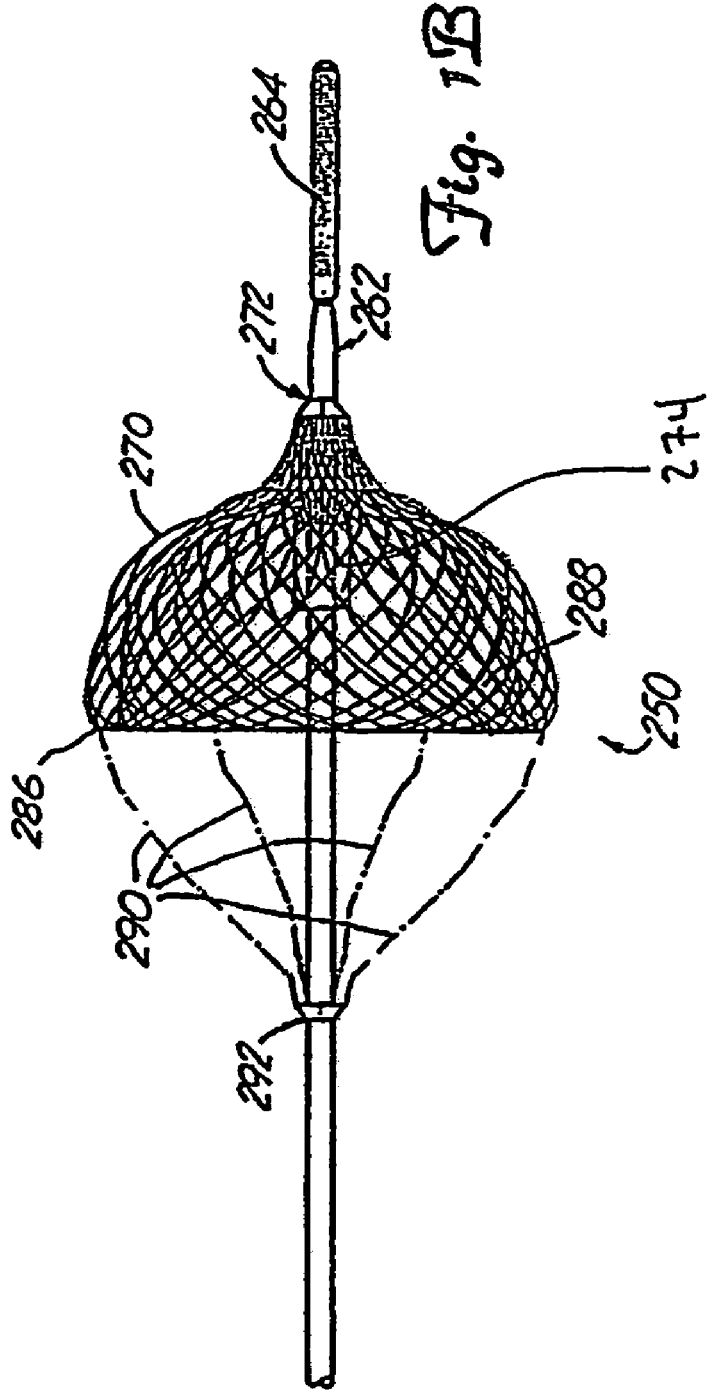

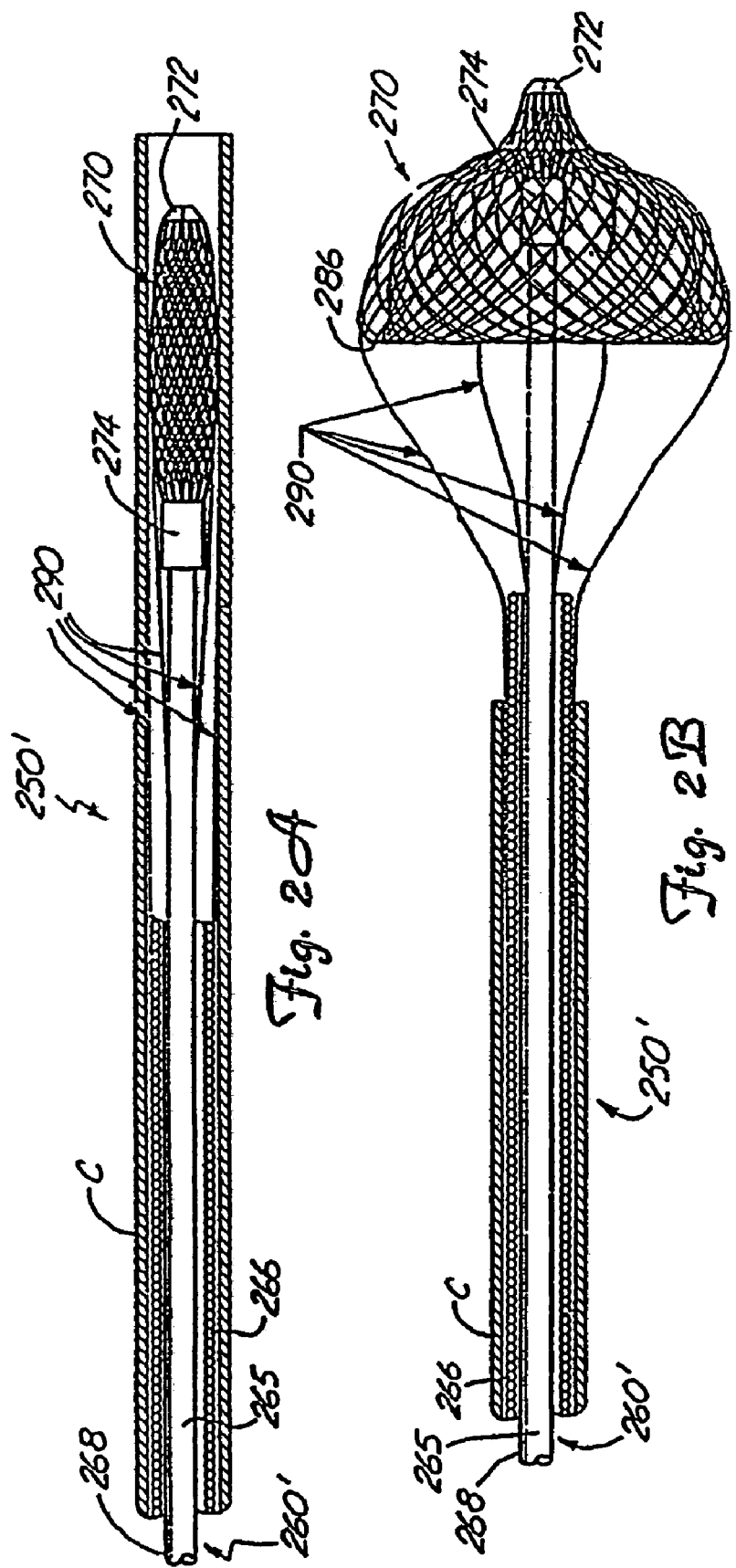

MINIMALLY INVASIVE MEDICAL DEVICE DEPLOYMENT AND RETRIEVAL SYSTEM

CROSS REFERENCE TO RELATED APPLICATION

The present application is a continuation of application Ser. No. 10/184,327, filed Jun. 27, 2002 now abandoned, which is a continuation of prior application Ser. No. 09/936,248, filed Jan. 28, 2002 now abandoned as a national stage filing under 35 U.S.C. § 371 of International Application No. PCT/US00/06212, filed on Mar. 8, 2000, which claims the priority date of provisional patent application U.S. Ser. No. 60/124,156, filed Mar. 8, 1999. Internatonal Application No. PCT/US00/06212 was published as WO 00/53120 on Sep. 14, 2000. The full disclosures of application Ser. No. 10/184,327, application Ser. No. 09/936,248, International Application No. PCT/US00/06212 and U.S. Ser. No. 60/124,156 are incorporated herein by reference.

FIELD OF THE INVENTION

The present invention generally relates to minimally invasive surgical procedures, e.g., angioplasty and atherectomy procedures, and has particular utility in connection with retrieving a medical device which has already been deployed. In one embodiment, the invention provides a vascular filter which can be retrieved with minimal risk of dumping the entrained contents back into the patient's bloodstream.

BACKGROUND OF THE INVENTION

In some medical procedures, a minimally invasive medical device is used to capture or dislodge material from within a patient's vascular system or other body vessel. For example, in certain procedures, balloon catheters are positioned such that the deflated balloon is placed distally of a vascular occlusion. Typically these vascular occlusions are relatively soft, uncalcified deposited along the walls of an artery. The balloon then may be inflated and drawn proximally. This will tend to dislodge any atheromatous material and withdraw it proximally with the balloon. In current procedures, an aspiration catheter will be moved distally into position adjacent the balloon and will be used to aspirate the dislodged material from the vessel.

A number of other minimally invasive surgical procedures are being used to treat vascular occlusions. These procedures include rotational atherectomy and balloon angioplasty. With the increasing use of vascular stents, it has been discovered that tissue or other material may build up inside a stent, reducing the patency of the vessel through the stent. In the course of improving the patency of the blood vessel utilizing these techniques, there is a risk that the material which was formally causing the obstruction within the vessel can simply float downstream with the flow of blood to the vessel. Accordingly, there is an increasing recognition of the value of taking steps to capture the dislodged material.

A number of researchers have proposed various traps or filters for capturing the particulate matter or other embolic particles let loose in such procedures. Some filters are permanently implanted within the vessel. Emboli trapped within the filter are either aspirated out of the interior of the filter or are dissolved using drugs. Other filters are intended to be temporary in nature, typically being removed after the angioplasty, atherectomy or other procedure is complete. Generally, the goal is to retract the filter with the thrombi trapped therein. Unfortunately, many designs of such temporary filters may get relatively difficult or complex to retract the trap back in to the catheter through which it was delivered without simply dumping the trapped thrombi back in to the bloodstream.

One particularly advantageous vascular filter is shown in co-pending U.S. patent application Ser. No. 08/272,425, and International Patent Application No. PCT/US95/08613, which was published as International Publication No. WO 96/01591, the teachings of which are specifically incorporated herein by reference.

FIGS. 11-16 of WO 96/01591 are attached hereto as FIGS. 1-6 of the present application. FIG. 1 is a vascular trap which is suitable for use in temporarily filtering embolic particles and the like from blood passing through a patient's vascular system. This device would most frequently be used to filter emboli from a patient's blood when another medical procedure is being performed, such as by using the trap in conjunction with a rotating cutting blade during an atherectomy, with a balloon catheter during angioplasty, or with a device used to clear the lumen of a stent during a stent cleaning procedure. It is to be understood, though, that the trap could also be used in other similar applications, such as in channels in patient's bodies other than their vascular systems.

The vascular trap 250 of FIGS. 1A and 1B comprises a generally umbrella-shaped basket 270 carried adjacent a distal end of a guidewire 260. The guidewire in this embodiment includes a tapered distal section 262 with a spirally wound coil 264 extending a distal length of the wire. Guidewires having such a distal end are conventional in the art. The basket 270 is positioned generally distally of the coil 264, and is desirably attached to the guidewire approximately with the proximal end of the tapered section as shown in these drawings.

The basket 270 of the device shown in WO 96/01591 (shown in its collapsed configuration in FIG. 1A) includes a distal band 272 and a proximal band 274. The distal band may be made of a radiopaque material, such as gold, platinum or tungsten, and is affixed directly to the shaft of the guidewire 260. This attachment may be made by any suitable means, such as by welding, brazing or soldering. Alternatively, the distal band 272 may comprise a bead of a biocompatible cementitious material, such as a curable organic resin. WO 96/01591 teaches that a radiopaque metal or the like can be imbedded in the cementitious material to increase the visibility of the band for fluoroscopic observation. The proximal band 274 may be formed of a hypotube sized to permit the tube to slide along the guidewire during deployment. The inventors of that prior application suggest that the hypotube be made of a metallic material; a thin-walled tube of a NM alloy should suffice. If so desired, the proximal band may be formed of a more radiopaque metal, or a NM alloy band can have a radiopaque coating applied to its surface.

As taught in some detail in WO 96/01591, the basket 270 taught therein is formed of a metal fabric. The metal fabric of this embodiment is optimally initially formed as a tubular braid and the ends of the wires forming the braid can be attached together by means of the bands 272, 274 before the fabric is cut to length. These bands 272, 274 will help prevent the metal fabric from unraveling during the forming process. (The method of forming the basket 270 is described in great detail in WO 96/01591 and this process is still believed to provide a suitable means for creating such a basket. The process is also discussed briefly below in connection with FIG. 6.).

When the device is in its collapsed state for deployment in a patient's vessel (as illustrated in FIG. 1A), the basket 270 of this device is said to be collapsed toward the axis of the guidewire 260. The distal 272 and proximal 274 bands are spaced away from one another along the length of the guidewire, with the fabric of the device extending therebetween. This publication teaches it is preferred that the basket is in its collapsed engages the outer surface of the guidewire to permit the device to be deployed through a relatively small lumen of a catheter or another medical device.

When the device is deployed in a patient's vascular system, the basket will take on an expanded configuration wherein it extends outwardly of the outer surface of the guidewire. As best seen in FIG. 1B, the shape of the basket 270 when deployed may generally resemble a conventional umbrella or parachute, having a dome-like structure curving radially outwardly from the guidewire moving proximally from the distal band 272. It is to be understood that other suitable shapes could easily perform the desired filtering function, such as a conical shape wherein the slope of the device changes more linearly than the smooth, rounded version shown in FIG. 1B. A relatively flat, disc shape may also suffice, but it is preferred that the device have a cavity or recess (discussed below) to better retain emboli or other material captured thereby. In this expanded configuration, the two bands 272, 274 are closer together, with the distal band 272 optimally being spaced only a short distance from the proximal band 274, as illustrated.

In moving from its collapsed state (FIG. 1A) to its expanded state (FIG. 1B), the metal fabric of this device turns in on itself, with a proximal portion 282 of the collapsed basket being received within the interior of a distal portion 284 of the collapsed basket. This produces a two-layered structure having a proximal lip 286 spaced radially outwardly of the guidewire, defining a proximally-facing cup-shaped cavity 288 of the basket. When blood (or any other fluid) flows through the basket in a distal direction, any particulate matter in the blood, e.g. emboli released into the bloodstream during atherectomy or angioplasty procedures, will tend to be trapped in the cavity 288 of the basket.

WO 96/01591 teaches that the precise dimensions of the metal fabric can be varied as desired for various applications. If the device 250 is to be used as a vascular filter to trap emboli released into the blood, for example, this reference teaches that the pores (i.e. the openings between the crossing metal strands) of the fabric are desirably on the order of about 1.0 mm. These inventors deemed this to be the minimum size of any particles which are likely to cause any adverse side effects if they are allowed to float freely within a blood vessel. They teach that the pores should not be too small, though, because the blood (or other fluid) should be free to pass through the wall of the basket 270. If so desired, the basket may be coated with a suitable anti-thrombogenic coating to prevent the basket from occluding a blood vessel in which it is deployed.

When a fabric having 1.0 mm pores is used to form this basket 270, the forming process reorients the wires relative to one another and in some areas (e.g. adjacent the proximal lip 286) the pores tend to be larger than 1.0 mm. However, because the baskets walls are formed of essentially two thicknesses 282, 284 of the fabric, the effective pore size of the device may be significantly reduced even at these locations.

The device 250 of FIG. 11 is also provided with tethers 290 for collapsing the basket 270 during retraction. The basket may include four independent tether wires, each of which extends proximally from the proximal lip 286 of the deployed basket. The authors suggested, though, that the four tether wires illustrated in the drawings be formed of two longer wires, with each wire extending peripherally about a portion of the proximal lip of the basket. These tether wires may be intertwined with the wires of the metal fabric to keep the tethers in place during use. When such tethers are retracted or drawn down toward the guidewire, the wires extending along the proximal lip of the basket will tend to act as drawstrings, drawing the proximal end of the basket radially inwardly toward the guidewire. This tends to close the basket and entrap any material caught in the cavity 288 of the basket during use so that the basket can be retracted without the use of a cover.

The tether wires 290 may extend along much of the length of the guidewire so that they will extend outside the patient's body during use of the device 250. When it is desired to collapse the basket for retrieval, the operator can simply hold the guidewire 260 steady and retract the tethers with respect to the guidewire. This can tend to be relatively cumbersome, though, and may be too difficult to effectively accomplish without breaking the tethers if the device is deployed at a selective site reached by a tortuous path, such as in the brain.

To address this issue, the authors suggest, as shown in FIGS. 1A and 1B, that the tethers 290 be attached to the guidewire 260 at a position spaced proximally of the basket. The tethers may, for example, be attached to a metal strap 292 or the like and this strap 292 may be affixed to the shaft of the guidewire. When it is desired to close the proximal end of the basket for retraction, they suggest urging an external catheter (not shown) distally toward the basket 270. When the catheter encounters the radially extending tethers, the distal end of the catheter will tend to draw the tethers toward the guidewire as the catheter is advanced, which will, in turn, tend to draw the proximal end of the basket closed.

FIGS. 2A and 2B illustrate an alternative embodiment of the device shown in FIGS. 1A and 1B, also in accordance with the teachings of WO 96/01591. FIG. 2A shows the device collapsed in a catheter C for deployment while FIG. 2B shows the device in its deployed configuration. In FIGS. 2A and 2B, the basket 270 is much the same as that outlined above in connection with FIGS. 1A and 1B. In the embodiment of FIG. 12, though, the distal band 272 is affixed to the guidewire 260' at the distal tip of the guidewire. The guidewire 260' is of the type referred to in the art as a "movable core" guidewire. In such guidewires, a core wire 265 is received within the lumen of a helically wound wire coil 266 and the core wire 265 extends distally beyond the distal end of the coil 266. A thin, elongate safety wire 268 may extend along the entire lumen of the coil 266 and the distal end of the safety wire may be attached to the distal end of the coil to prevent loss of a segment of the coil if the coil should break.

In the embodiment of FIGS. 1A and 1B, the proximal ends of the tethers 290 are attached to a metal strap 292 which is itself attached the shaft of the guidewire 260. In FIGS. 2A and 2B, the tethers are not attached to the core wire 265 itself. Instead, the tethers are attached to the coil 266 of the guidewire. The tethers may be attached to the coil by any suitable means, such as by means of laser spot welding, soldering or brazing. The tethers 290 may be attached to the coil 266 at virtually an spot along the length of the coil. As illustrated in these drawings, for example, the tethers may be attached to the coil adjacent the coil's distal end. However, if so desired the tethers may be attached to the coil at a location space more proximally from the basket 270.

An external catheter such as that referred to in the discussion of FIG. 1A, but not shown in that figure, is illustrated in FIGS. 2A and 2B. Once the basket 270 is deployed in a patient's vessel to substantially reach the expanded configuration shown in FIG. 2B and the basket has performed its intended filtration function, the external catheter C can be urged distally toward the basket 270. As this catheter is urged forward, the tethers will tend to be drawn into the distal end of the catheter, which is substantially narrower than the proximal lip 286 of the basket. This will tend to draw the tethers down toward the guidewire and help close the basket, as explained above.

FIGS. 3-5 illustrate yet another alternative embodiment of a vascular trap in accordance with WO 96/01591. This vascular trap 300 includes a basket 320 received over a guidewire 310. In most respects, the basket 320 is directly analogous to the basket 270 illustrated in FIGS. 1-2. The basket 320 includes a proximal band 322 and a distal band 324. As in the device of FIGS. 2A and 2B, the distal band may be attached to the guidewire adjacent is distal end. If so desired, though, a structure such as is shown in FIGS. 1A and 1B, wherein the guidewire extends distally beyond the basket, could instead be used.

As best seen in its collapsed state (shown in FIG. 3), the basket includes a distal segment 325 and a proximal segment 326, with the distal end of the distal segment being attached to the distal band 324 and the proximal end of the proximal segment being attached to the proximal band 322. When the basket 320 is in it expanded configuration (shown in FIG. 4), the proximal segment 326 is received within the distal segment 325, defining a proximal lip 328 at the proximal edge of the device. The wall of the basket thus formed also includes a cavity 329 for trapping solids entrained in a fluid, such as emboli in a patient's blood stream.

The basket 320 of FIGS. 3-5 is also shaped a little bit differently than the basket 270 of the previous drawings. The primary difference between these two baskets is that the basket 320 is a little bit shorter along its axis that is the basket 270. This different basket shape is simply intended to illustrate that the basket of a vascular trap in accordance with the invention can have any of a wide variety of shapes and no particular significance should be attached to the slightly different shapes shown in the various drawings.

In the vascular traps 250 and 250' of FIGS. 1 and 2, respectively, tethers were used to draw down the proximal end of the basket 270 to dose the basket for retraction. In the embodiment shown in FIGS. 3-5, though, the trap 300 includes a basket cover 340 positioned proximally of the basket 320. The basket cover may also be formed of a metallic tubular braid and is also adapted to be collapsed to lay generally along the outer surface of the guidewire 310. The cover 340 is not directly affixed to the guidewire at any point, though, but is instead intended to be slidable along the guidewire. As best seen in FIGS. 3 and 4 wherein the cover is In its collapsed state, the cover 340 includes a distal hypotube 342 and a proximal control hypotube 344, with the distal hypotube being attached to the distal end of the cover 340 and the proximal control hypotube 344 being attached to the proximal end of the cover.

The cover 340 is shown in its deployed, expanded configuration in FIG. 5. As shown in that figure, the cover has a similar structure to that of the basket 320, but is oriented to be open distally rather that proximally, as is the basket. As best seen in FIGS. 3 and 4 wherein the cover is in its collapsed state, the cover has a distal segment 352 and a proximal segment 354. When the cover is deployed by urging it distally out of the distal end of the deployment catheter C, the cover 340 will tend to resiliently return to Its expanded configuration and the distal hypotube 342 will slide axially proximally along the guidewire toward the proximal control hypotube 344. This will invert the collapsed cover so that the distal section 352 is generally received within the proximal section 354, defining a distal lip 358 of the cover.

WO 96/01591 teaches that the proximal control hypotube 344 of this cover may extend along a substantial portion of the length of the catheter 310 so that it extends out of the patient's body when the device 300 is in place. By grasping the control hypotube and moving it relative to the guidewire 310, an operator can control the position of the cover 340 with respect to the basket 320, which is affixed to the guidewires. As explained in more detail below in connection with the use of the device 300, once the basket has been deployed and has been used to filter objects entrained in the fluid (e.g. emboli in blood), the cover 340 may be deployed and the trap may be drawn proximally toward the cover by moving the guidewire proximally with respect to the control hypotube 344.

The inner diameter of the distal lip 358 of the cover is desirably slightly larger than the outer diameter of the proximal lip 328 of the basket. Hence, when the basket is drawn proximally toward the cover it will be substantially enclosed therein. The cover will therefore tend to trap any emboli (not shown) or other particulate matter retained within the cavity 330 of the basket. A retrieval sheath S may then be urged distally to engage the outer surface of the cover 340. This will tend to cause the cover to collapse about the basket, tightly engaging the outer surface of the basket. This somewhat collapsed structure can then be withdrawn from the patients channel and removed from the patient's body. By enclosing the basket within the cover, the likelihood of any filtered debris within the basket being lost as the basket is retrieved will be substantially eliminated.

FIG. 6 illustrates the molding element 370 suggested in WO 96/01591 for use in making a basket 270. Although the basket 320 and cover 340 of the trap 300 are shaped somewhat differently, an analogous molding element can be used for these portions of the trap 300 as well by simply modifying some of the dimensions of the molding element 370, but retaining the basic shape and structure of the molding element. It also should be understood that the molding element 370 is merely one possible molding element for forming a shape such as that of the basket 270 and WO 96/01591 teaches a variety of different molding elements and notes that other designs will be apparent to those skilled in the art.

The molding element 370 of FIG. 6 has an outer molding section 372 defining a curved inner surface 374 and an Inner molding section 376 having an outer surface 378 substantially the same shape as the curved inner surface 374 of the outer molding section. The inner molding section 376 should be sized to be received within the outer molding section, with a piece of the metal fabric (not shown) being disposed between the inner and outer molding sections. In a preferred embodiment, the inner surface 374 of the outer molding element and the outer surface 378 of the inner molding section each include a recess (375 and 379, respectively) for receiving an end of the braid. The molding surface of this molding element 370, to which the fabric will generally conform, can be considered to include both the inner surface 374 of the outer molding section and the outer surface 378 of the inner molding section.

WO 96/01591 teaches that the two molding sections 372, 376 are spaced apart from one another and a length of a tubular braid of metal fabric (not shown in FIG. 6) Is disposed between these molding sections. Optimally, one end of the fabric is placed in the recess 375 of the outer molding section and the other end of the fabric is placed in the recess 379 in the inner molding section. As noted above, the ends of the tubular fabric can be clamped prior to this molding process to limit the likelihood that the fabric will unravel. The inner and outer molding sections can then be urged generally toward one another. As the ends of the wire approach one another, the tubular braid will tend to invert upon itself and a surface of the tubular braid will generally conform to either the inner surface 374 of the outer molding section or the outer surface 378 of the inner molding section, arriving at a shape analogous to that of the basket 270 of the traps 250, 250'. The two molding sections can them be locked in place with respect to one another and the metal fabric may be heat treated to set the wires in this deformed configuration.

This published international application also teaches how one may use the traps 250, 250' and 300 taught therein. It suggests that these traps be deployed for use in conjunction with another medical device and that they will most frequently be retracted from the patient's body after use. WO 96/01591 uses a balloon angioplasty procedure and an atherectomy procedures as contexts for illustrating a method of using such traps. In balloon angioplasty, balloon catheters having inflatable balloons at their ends are positioned within a blood vessel so that the balloon is positioned within a stenosis. These balloons are positioned by tracking the balloon catheter along a guidewire or the like; the balloons typically have a central bore therethrough. Once the balloon is properly positioned, it is inflated and urges radially outwardly against the stenosis. This will tend to squeeze the stenosis against the walls of the vessel, improving patency of the vessel.

When the stenosis is treated in this fashion, though, there is a risk that some debris will break free and enter the blood flowing through the vessel. If left unchecked, this embolus can drift downstream and embolize a distal portion of the vessel. Depending on where the embolus comes to rest, the embolization can result in significant tissue or organ damage. In order to prevent, or at least substantially limit, such embolization, WO 96/01591 suggests the use of a vascular trap 250, 250' or 300 of with the balloon catheter. The device should be sized to permit it to be passed through the lumen of the particular balloon catheter to be used in the angioplasty.

In one method taught in WO 96/01591, the trap is deployed first. The basket (270 or 320) of the trap is guided to a position located downstream of the desired treatment site through an introduction catheter (e.g. the catheter C in FIGS. 12-15). The basket is then urged distally beyond the end of the catheter, which permits the basket to resiliently substantially return to its expanded configuration from its collapsed configuration within the catheter. Once the trap is in place, the balloon catheter can be exchanged for the introduction catheter, and the balloon catheter can track the guidewire (260 or 310) of the vascular trap. The balloon can then be positioned within the stenosis and expanded, as outlined above. Once the angioplasty has been completed, the balloon can be deflated again and withdrawn proximally out of the patient.

WO 96/01591 also explains that the balloon catheter can be used to perform the same function as performed by the introduction catheter in the preceding embodiment. In this embodiment, the balloon catheter is positioned in the patient's vessel so that the distal end of the balloon catheter is located downstream of the stenosis. The vascular trap (250, 250' or 300) of the invention is then passed through the lumen of the balloon catheter and the basket is urged out of the distal end of the catheter. The basket will resiliently substantially return to its preferred expanded configuration, whereupon the balloon catheter can be retracted along the shaft of the device's guidewire until the balloon is properly positioned within the stenosis.

If so desired, the balloon catheter can instead be provided with a length of standard catheter extending distally beyond the distal end of the balloon. The balloon can then be positioned within the stenosis and the basket can be urged out of the distal end of the distal extension of the catheter. In such an embodiment, the length of the distal extension of the catheter should be sufficient to properly position the basket with respect to the balloon when the basket exits the distal end of the catheter. This will eliminate the need to perform the separate step of retracting the balloon into position within the stenosis after the basket is deployed. The balloon can then be expanded, deflated and withdrawn as described above.

WO 96/01591 teaches that much the same procedure can be used to deploy a vascular trap for use in an atherectomy procedure. In such procedures, a cutting head is positioned at the distal end of an elongate, hollow shaft and the cutting head has a bore extending therethrough. The trap can be deployed in either of the methods outlined above, but it is anticipated that in most instances the first procedure will be used, i.e. the basket will be deployed with an introduction catheter, which will be removed so that the cutting device can be guided over the guidewire of the vascular trap. This publication also stresses that the device 250, 250' and 300 could be used in other medical procedures in other bodily channels besides a patients vascular system.

Since the trap is positioned downstream of the stenosis, any debris released during one of these procedures will tend to drift distally toward the basket and be caught therein. In order to prevent any emboli from simply floating past the trap, it is preferred that the proximal lip (288 or 328) of the basket be at least as large as the lumen of the vessel. WO 96/01591 suggests that the natural dimension of the proximal lip (i.e. where the basket has fully returned to its expanded configuration) be made somewhat greater than the vessel's inner diameter so the basket will firmly engage the wall of the vessel.

The method of retracting the basket will depend on which embodiment of the vascular trap is used, namely whether or not the device includes a cover 340. The device 250 or 250' of FIG. 1 or 2, respectively, do not include such a cover. However, they do include tethers 290 which extend proximally from the proximal lip 288 of the basket to an attachment to the guidewire. In either of these embodiments, a retrieval catheter can be introduced over the guidewire and urged distally toward the basket. As explained above in connection with FIGS. 1 and 2, this will tend to draw the tethers down toward the guidewire, effectively closing the proximal end of the basket 270. Once the basket is sufficiently dosed, such as when the proximal lip of the basket engages the distal tip of the retrieval catheter, the catheter and the vascular trap can be retracted together from the patient's body. By substantially closing the proximal end of the basket in such a fashion, any emboli which are captured in the basket when it is deployed can be retained within the basket until it is removed from the patient's body.

If so desired, a balloon catheter or like device can instead be used, with the balloon catheter being used to draw down the tethers 290 and collapse the basket. The vascular trap can then be withdrawn with the balloon catheter rather than having to separately introduce a removal catheter to remove the trap.

In withdrawing the embodiment illustrated in FIGS. 3-5, the cover 340 is positioned over the proximal lip of the basket before the vascular trap 300 is retracted. Once the medical procedure is completed and any debris has been captured in the basket, the cover 340 is allowed to resiliently substantially return to its expanded configuration. Once it is deployed proximally of the basket, the basket 320 can be drawn proximally toward the cover 340 until it engages or is received within the cover, as noted above in connection with FIG. 5.

In actuality, the cover 340 of FIGS. 3-5 may be unable to return to its full expanded configuration due to the confines of the vessel in which it is deployed. As explained previously, the cover 340 is desirably larger than the basket 320 so that the basket can be received within the cover. However, the basket is optimally sized to engage the walls of the vessel to prevent the unwanted passage of emboli or other debris around the edges of the basket. Accordingly, the distal lip 358 of the cover will engage the wall of the channel before it expands to its full size. The walls of most bodily channels, such as blood vessels, tend to be somewhat elastic, though. The cover 340 will therefore tend to urge harder against the wall of the vessel than the smaller basket and may stretch the vessel a little bit more than will the basket. In this fashion, the cover may still be able to expand to a dimension large enough to permit the basket to be received in the cavity 356 of the cover. If not, the distal lip 358 of the cover can simply be brought into close engagement with the proximal lip 328 of the basket to generally seal the basket.

Once the cover 340 is brought into engagement with the basket 320, whether by receiving the basket within the cover or, less preferably, by engaging the lips 358, 328 of the cover and the basket, the device can be withdrawn proximally from the patient's vascular system. The cover will tend to prevent any emboli caught in the basket during deployment from being inadvertently lost during withdrawal.

The vascular traps 250, 250' and 300 shown in FIGS. 1-6 represent a significant advancement over previously available devices. The embodiment of FIGS. 3-5 shows particular promise in that the cover permits the user to withdraw the basket with the emboli entrained therein without having to take any additional precautions to minimize the chances that these emboli will be accidentally dumped back into the bloodstream.

SUMMARY OF THE INVENTION

The present invention provides a medical device retrieval system and a method of retrieving a medical device. In accordance with one embodiment of the invention, a medical device retrieval system includes a medical device and a retrieval cover. The medical device comprises a working element carried by a flexible, elongate shaft. The working element has a proximal profile and the shaft extends proximally from the working element. The retrieval cover is slidably carried along the shaft of the medical device. The cover has a deployed configuration and is capable of being compressed in a compressed configuration for deployment, yet resiliently substantially returned to the deployed configuration. The cover in its deployed configuration has a radially reduced proximal portion. A distally open distal end defining a distal opening having a maximum dimension at least as great as the maximum dimension on the proximal profile of the working element of the medical device, and an elongate internal recess defined between the proximal portion on the distal end. The cover in its compressed configuration is radially compressed inwardly toward the shaft and is distally open, with the distal end defining the distal-most portion of the cover. Optimally, the retrieval cover is designed to maintain this general orientation wherein the distal end of the device is always the distal-most portion of the cover, regardless of the configuration of the device.

This medical device retrieval system may further include a retrieval sheath which is slidable along the shaft of the medical device. Such a sheath, if included, is desirably positioned distally on the cover when the cover is in its deployed configuration. This retrieval sheath may have an inner diameter smaller than the outer diameter of the cover in its deployed configuration. This sheath is adapted to slide distally along the cover to compress the cover about the medical device.

In accordance with a further embodiment, the present invention provides a medical device retrieval system which comprises a medical device, a retrieval sheath, a deployment stylet and a retrieval cover. The medical device comprises a working element carried by a flexible, elongate shaft having an outer diameter. The working element has a proximal profile and the shaft extends proximally from the working element. The retrieval sheath is slidable along the shaft of the medical device and optimally has a beveled distal end with a distal lumen. The deployment stylet is slidable along the shaft of the medical device and has a distal tip. This distal tip tapers distally from a first diameter approximating the diameter of the distal lumen of the sheath to a second diameter more closely approximating the outer diameter of the medical device shaft. This provides a transition between the shaft of the medical device and the distal end of the retrieval sheath when the deployment stylet is positioned such that a distal tip extends distally beyond the distal end of the retrieval sheath. The retrieval cover is slidable along the shaft of the medical device and is exchangeable for the stylet along that shaft. The cover has a deployed configuration and is capable of being compressed into a compressed configuration for sliding within the lumen of the retrieval sheath yet resiliently substantially return to the deployed configuration. In its deployed configuration, the cover has a radially reduced proximal portion, a distally open distal end, and an elongate internal recess defined between the proximal portion and the distal end. The distal end defines a distal opening having a maximum dimension at least as great as the maximum dimension of the proximal profile of the working element of the medical device. In its compressed configuration, the cover is radially compressed inwardly toward the shaft and is distally open, with the distal end defining the distal-most portion of the cover.

Another embodiment of the invention provides a retractable medical device system including a medical device, a retrieval cover and a retrieval sheath. The medical device comprises a working element carried by a flexible, elongate shaft. The retrieval cover is slidable along the shaft of the medical device. The cover has a radially reduced proximal portion, a distally open distal end an elongate tubular wall extending therebetween and defining a recess. The working element of the medical device is completely retained within the recess of the cover such that the tubular wall extends distally beyond the medical device. The retrieval sheath has a lumen and is slidable with respect to both the medical device and the cover. At least a proximal length of the working element of the medical device and the cover are retained within the lumen of the retrieval sheath, with the retrieval sheath regularly compressing the proximal length of the cover such that an intermediate portion of the wall tightly engages the surface of the medical device. This will tend to effectively trap any emboli or other materials retained by the medical device.

As noted above, the present invention contemplates a method. One such method involves receiving particulate or other form material within a channel of a patient's body. As a first step in performing this method, one provides a medical device having a working element and a flexible, elongate shaft adapted to follow a path within the channel; a distally open cover slidable with respect to the shaft; and a retrieval sheath movable with respect to the cover on the shaft. The medical device is positioned within the vessel to engage a wall of the channel and trap the material within the channel. Either during such positioning or after the medical device has been positioned and while it is trapping material within the channel, the cover and the retrieval sheath may be positioned so they are spaced proximally of the working element along the shaft of the medical device. The cover is radially compressed within the lumen of the retrieval sheath such that it has a distally open distal end and a wall defining a recess, the wall engaging an inner surface of the retrieval sheath. The cover is moved distally with respect to the retrieval sheath, thereby permitting the cover to radially expand into a deployed configuration wherein the distal end remains distally open and the enclosure is radially expanded. The cover expands radially outwardly into the deployed configuration without having to invert on itself. The cover is then moved distally into engagement with a surface of the medical device to form therebetween an enclosure. The retrieval sheath may then be moved distally with respect to the cover to urge to cover to collapse about the medical device and tightly engage the surface of the medical device.

BRIEF DESCRIPTION OF THE DRAWINGS

FIG. 1A is a schematic side view in accordance with WO 96/01591, showing a vascular trap in a collapsed state for deployment in a patient's vascular system;

FIG. 1B is a schematic side view of the medical device of FIG. 1A in an expanded state for deployment in a patient's vascular system;

FIG. 2A is a schematic side view in accordance with WO 96/01591, showing an alternative vascular trap in a collapsed state within a catheter for deployment;

FIG. 2B is a schematic side view of the device of FIG. 2A, showing the device deployed distally of the catheter;

DETAILED DESCRIPTION OF THE PREFERRED EMBODIMENTS

Figure 8:
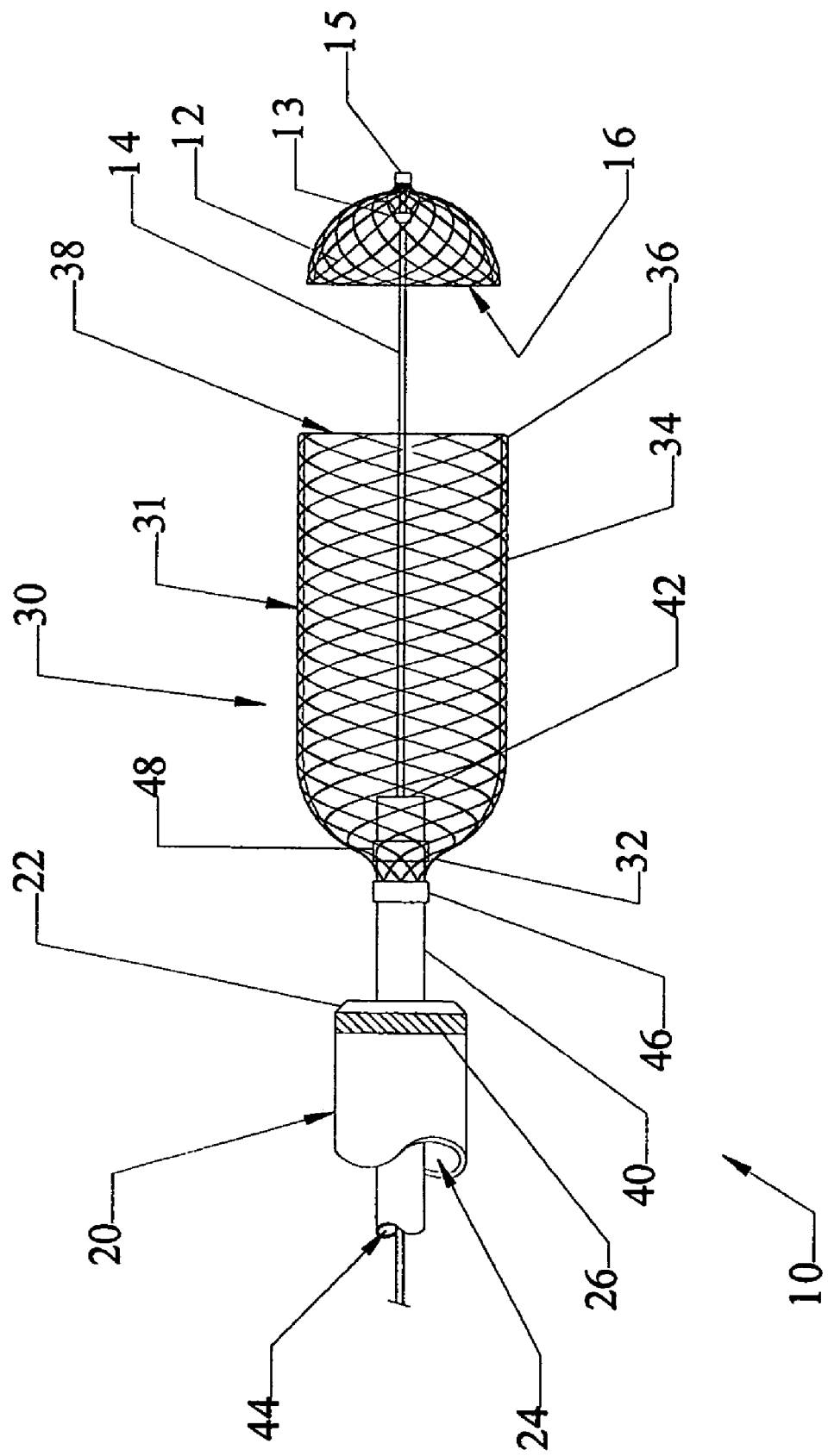
FIG. 8 is a schematic side view of a device in accordance with the present invention with both the trap and the cover fully deployed.

FIGS. 8-12 schematically illustrate the operation of one embodiment of the present invention. FIG. 8 illustrates certain operative portions of the medical device retrieval system 10 of the invention in a fully deployed state. As noted above, the retrieval system of the invention is intended to be used in connection with a medical device having a working element carried by flexible, elongate shaft. In these drawings, the medical device is typified as a vascular trap similar to the vascular trap 250 of FIG. 11, but omitting the tethers 290. The working element of this medical device is a basket 12, which may be substantially as outlined above in connection with the description of the basket 270. The shaft in this design may simply comprise a guidewire 14. While the construction and operation of the basket 12 may be substantially the same as that outline for the baskets shown in FIGS. 1-5, it is generally preferred that the proximal band 13 of this basket be attached to the guidewire while the distal band 15 be permitted to slide along the guidewire. Hence, when the basket 12 is released from a delivery catheter and the basket is allowed to achieve a radially expanded configuration, the distal end of the collapsed device (272 in FIG. 1A) will slide approximately toward the proximal end (274) of the collapsed device.

It should be recognized that the medical device can be varied as desired. For example, the medical device used in connection with the present retrieval system could instead by a balloon catheter, wherein the working element would be the balloon portion of the catheter and the shaft would comprise the body of the catheter extending proximally of the balloon.

The other elements of the retrieval system 10 generally comprise a retrieval sheath 20 and a cover 30. It is to be understood that these drawings are intended merely for illustrative purposes and are not drawn to scale. In actual operation, the retrieval sheath 20 and the shaft 40 of the cover would likely be much smaller. These elements are simply drawn larger to make the various components easier to see in the attached illustrations.

The cover 30 includes a radially expandable body 31 carried by a shaft 40. The body has a proximal portion 32 which is radially compressed into close proximity with the shaft 40 and is desirably attached directly thereto. A tubular wall 34 extends distally from the proximal portion and terminates in a distally open end 36. The body 31 defines a recess 38 within which the working element of the medical device may be retracted, as explained more fully below. The majority of the length of this recess is defined by the generally tubular wall 34.

This radially expandable body 31 can be formed of any suitable material. As explained more fully below, it is preferred that this body be capable of being collapsed within the retrieval sheath 20 for deployment, radially expand into a deployed configuration, yet be readily collapsed by the retrieval sheath to tightly engage the working element of the medical device. Any material which achieves this function may be used.

In one embodiment (not shown), the body 31 is formed of a flexible plastic material, which may be reinforced with one or more flexible metal hoops or the like to bias the tubular plastic member into a funnel-like configuration.

The illustrated embodiment is shown as comprising a series of flexible metal wires. As explained in some detail in International Publication No. WO 96/01591, such a radially expandable device may be made rather conveniently utilizing a metal fabric having strands formed of a material which is both resilient and which can be heat treated to substantially set a desired shape. Materials such as elgiloy, hastelloy, incoloy, certain grades of stainless steel and shape memory alloys. Of these materials, shape memory alloy such as nitinol are particularly preferred.

In one useful embodiment, the radially expandable body 31 is formed using the techniques outlined in WO 96/01591, starting with a metal fabric comprising both nitinol and platinum. For example, the fabric may be a generally tubular fabric formed of 48 wires having a diameter on the order of about 0.0015 inches and a pic rate of about 80-100 pics per inch. Of the 48 wires used to form this metal fabric, a relatively small percentage of the wires (e.g. 4-6 wires) may be formed of platinum or some other relatively radiopaque material to enhance visibility of the device on a fluoroscope without unduly affecting the resiliency of the fabric. If so desired, the wires can be coated with a therapeutic agent or with an antithrombogenic material. For example, the wires may be coated with heparin or with a known platelet-deactivating drug, e.g., a 2B-3A antagonist.

This radially expandable body 31 is carried by a axially slidable shaft 40. This shaft may take the form of a metallic hypotube, such as that discussed in connection with the embodiment of FIGS. 3-5. More preferably, though, the shaft 40 comprises a flexible plastic material of the type that is commonly used in forming medical catheters. If friction of this shaft 40 with the retrieval sheath 20 and/or the shaft 14 of the medical device is anticipated to present a problem, this shaft 40 of the cover may be formed of polytetrafluoroethylene or another suitable low-friction material.

The radially expandable body 31 may be attached to the shaft 40 in any suitable manner. Presumably, the ends of the wires defining the body 31 could be simply cast into the plastic defining the flexible shaft 40. However, the embodiment shown in the drawings is somewhat easier to make, utilizing a pair of marker bands 46 and 48 to attach the body to the shaft by damping the proximal end about the exterior of the sheath. Forming these clamps of a radiopaque material will make it easier to track the position of the cover 30 as it is deployed. In the illustrated embodiment, the cover comprises an exterior layer and an interior layer of the metal fabric, much like the basket 270 described above in connection with FIGS. 1-5. In this configuration, the proximal marker band 46 may be used to damp the exterior layer of the metal fabric to the exterior of the shaft 40 while the distal marker band 48 is used to clamp the interior layer of the fabric to the shaft.

In the illustrated embodiment, the shaft 40 includes a lumen 44 through which the shaft 14 of the medical device is received, thereby permitting the cover 30 to track that shaft for deployment. The shaft 40 shown in FIGS. 8 and 9 extends distally beyond the distal marker band 48 such that the distal tip 42 of the shaft is received within the recess 38 of the cover. Not only will this make manufacturing easier, but it will reduce the likelihood that any guidewire or other device passing through the lumen 44 of the shaft 40 will get caught up in the metal fabric defining the radially expandable body 31.

The retrieval sheath 20 may simply take the form of a standard medical catheter, with a tip as described below. This sheath has a generally tubular wall defining a lumen 24 within which the shaft 14 of the medical device and the shaft 40 of the cover may be slidably received. The differences in the diameters of these three elements 20, 40 and 14 are exaggerated in FIGS. 8 and 9 to illustrate operation of the device. In reality, these diameters would likely be substantially closer than those shown.

The distal tip 22 of the retrieval sheath 20 may be beveled to produce a smoother tip. (The advantage of this tip construction will be highlighted below in connection with the discussion of FIGS. 7, 13 and 14.) If so desired, a marker band 26 may be incorporated into the wall of the retrieval sheath 20 adjacent the distal tip 22. This will help an operator visualize the relative position of the retrieval sheath 20, the cover 30 and the basket 12 during operation.

Figure 9:
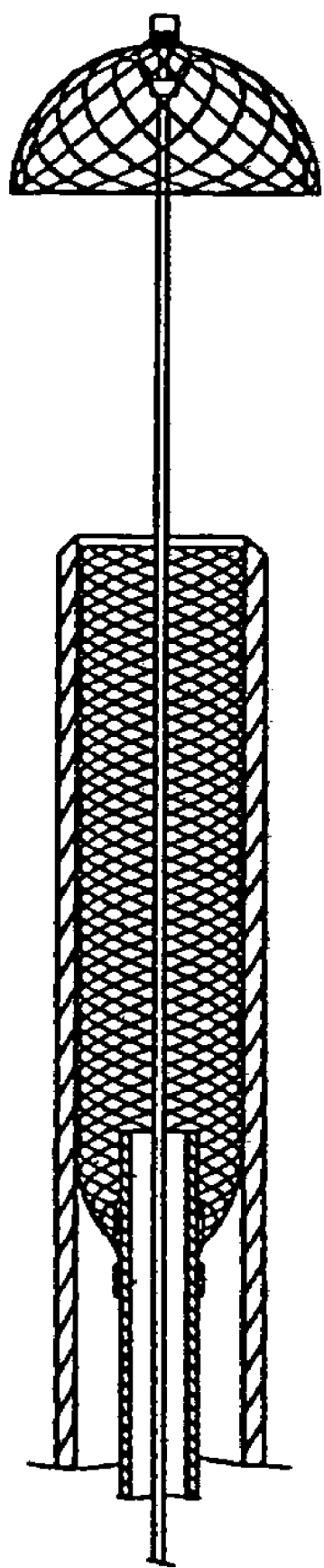
FIG. 9 is a schematic cross sectional view showing the device of FIG. 8 wherein the trap has been deployed but the cover has retained within the retrieval sheath.

FIG. 9 is a schematic cross sectional view of the device illustrated in FIG. 8 prior to deployment of the cover. In operation, the medical device will typically be put in place first. As outlined above in connection with FIGS. 1 and 2, the basket 12 may be positioned distally of a particular treatment site and the treatment device (e.g. a balloon catheter or an atherectomy device) can be guided over the shaft 14 of the trap to perform the intended procedure. In the use of the retrieval system of the invention with such a trap, one would typically deploy the retrieval sheath 20 and the cover 30 after the basket 12 has been in place for some time rather than deploying all three elements at substantially the same time. It should be understood, though, that simultaneous deployment may be appropriate in other circumstances, such as when a cover 30 and retrieval sheath 20 are used in connection with a Foley catheter or the like.

Whereas FIG. 8 illustrates the cover in its deployed configuration, FIG. 9 illustrates the cover in a compressed configuration which is suitable for deployment. Even in its compressed configuration, it can be seen that the body 31 of the catheter generally includes a radially reduced proximal portion 32, an elongate tubular wall 34 and a distally open distal end 36 which defines the distal-most portion of the cover. This is indirect contrast to the structure shown in FIGS. 3 and 4, which show the cover 340 of that device in its collapsed state. In this collapsed state, the cover 340 has a distal segment 352 and a proximal segment 354, both of which are generally tubular in shape and lie proximate the exterior surface of the guide wire 310. Once this cover is deployed as shown in FIG. 5, though, the cover must invert on itself to position the distal section 352 generally within the proximal section 354 to define a distal lip 358 of the cover. This distal lip 358 is merely an intermediate point along the longer, axially expanded configuration of the device when it is collapsed, as shown in FIGS. 3 and 4.

Figure 3:
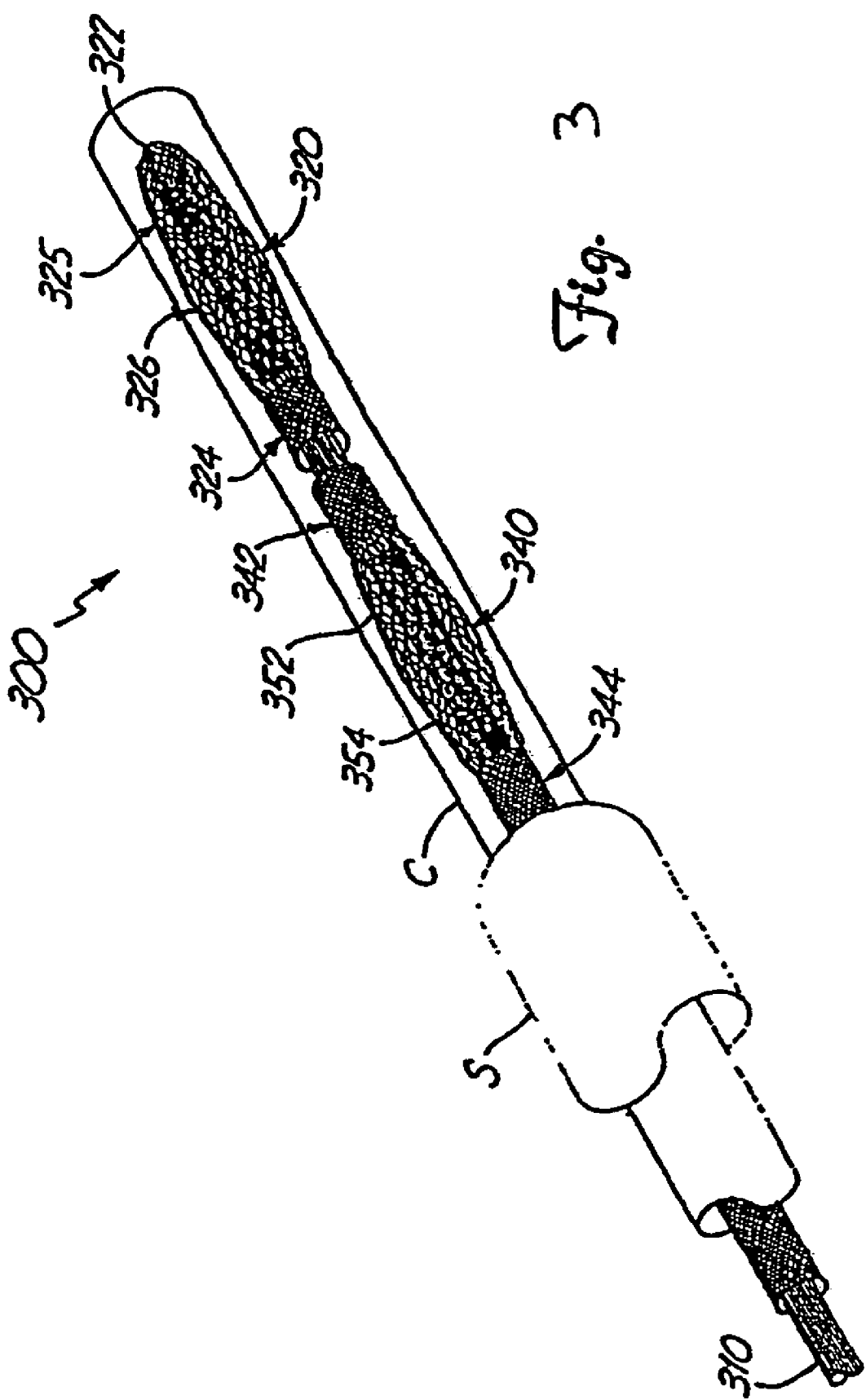
FIG. 3 is a schematic perspective view in accordance with WO 96/01591 showing a vascular trap and a cover, both of which are collapsed within a catheter for deployment in a channel in a patient's body.
Figure 4:
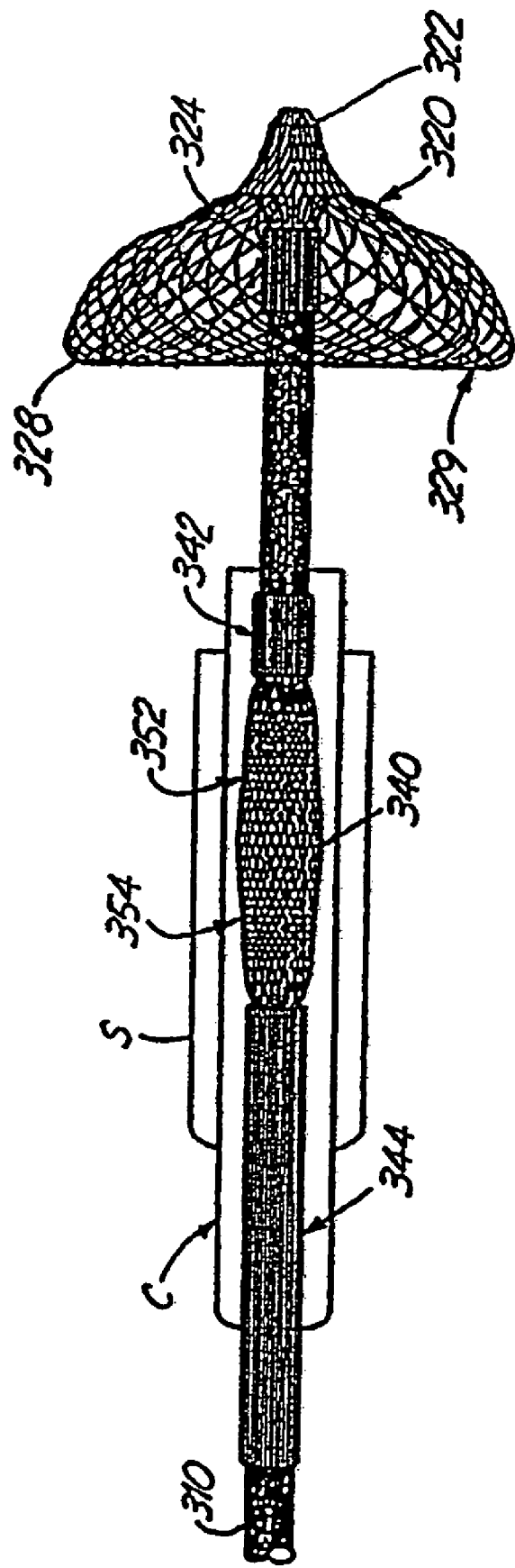
FIG. 4 is a schematic side view of the device of FIG. 3 in a partially deployed state, wherein the vascular trap has been deployed, but the cover is still collapsed within the catheter.
Figure 5:
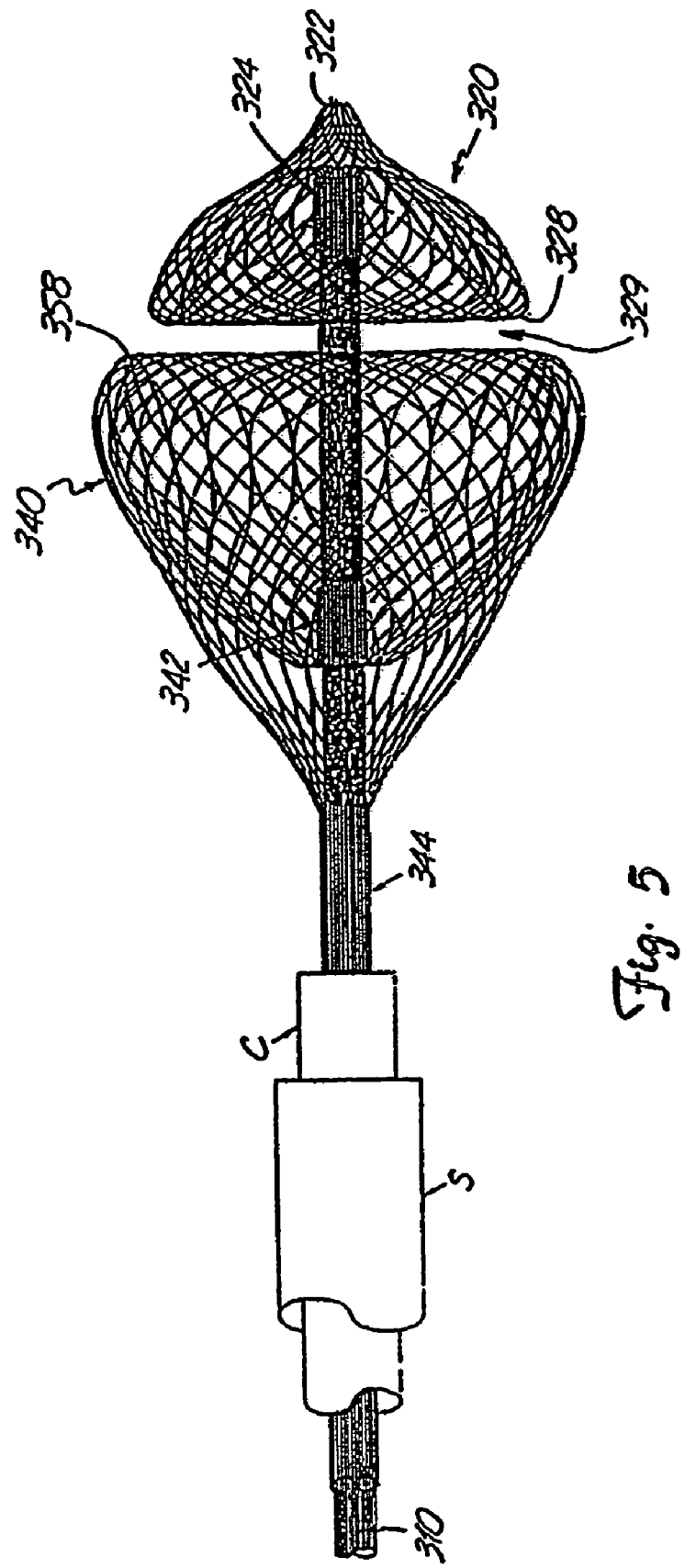
FIG. 5 is a schematic side view of the device of FIG. 3 in a fully deployed state.
Figure 6:
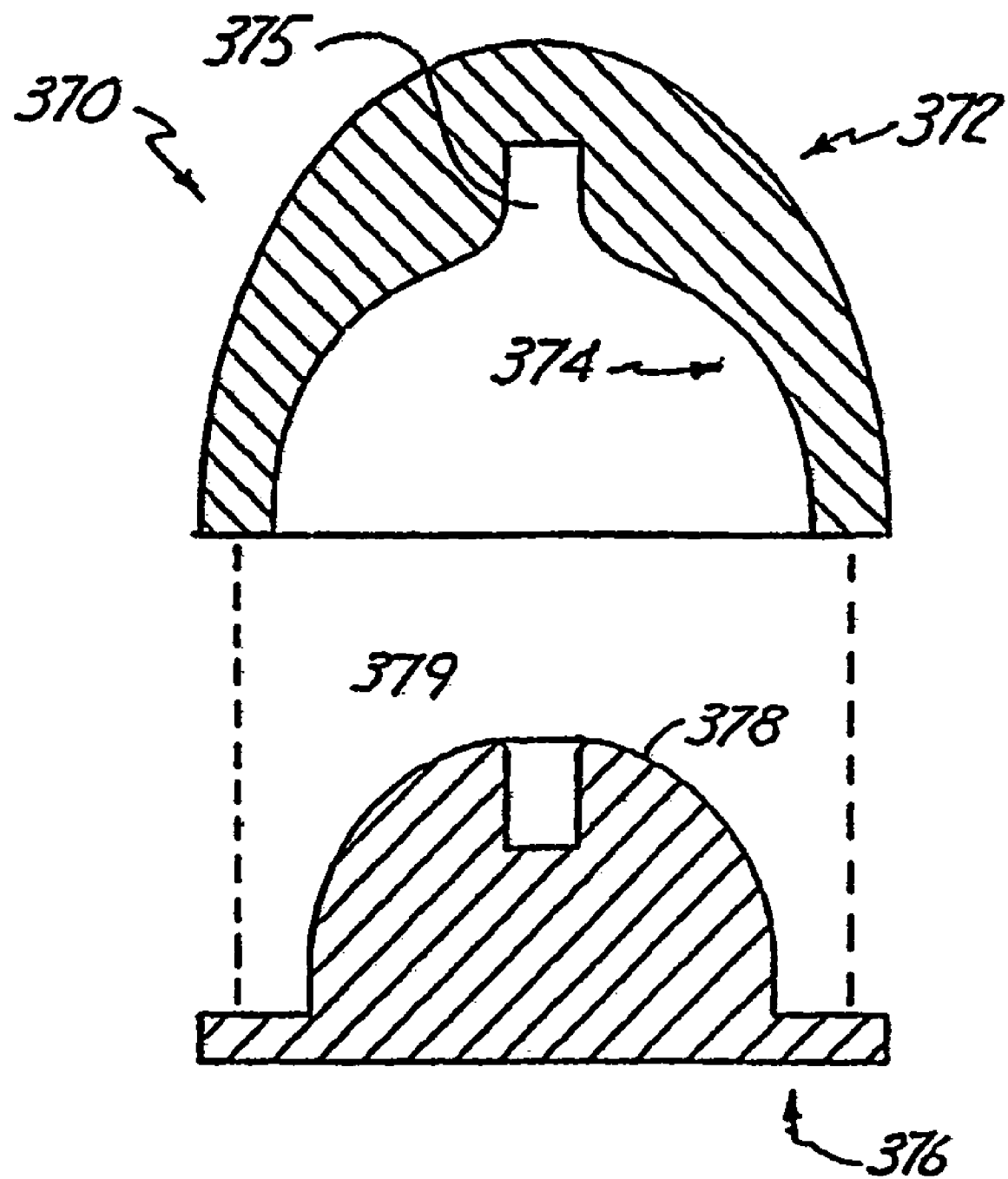
FIG. 6 illustrates one embodiment of a molding element which may be used in making a portion of the vascular traps shown in FIGS. 1-5.

There are a number of advantages of the structure of the present cover 30 over the mechanically more complex design of FIGS. 3-5. In the cover 340 of FIGS. 3-5, the cover must invert on itself before it can be used to enclose the basket 320. The resilient nature of the metal fabric used to form the cover 340 will tend to resiliently draw the distal hypotube 342 proximally toward the proximal control hypotube 344 once the constraint of the deployment catheter C has been removed.

The walls of the vessel can hinder complete inversion of the cover 340, though. In particular, if the inner diameter of the vessel within which the cover is to be deployed is significantly smaller than the outer diameter of the fully deployed cover, the cover may take on a sausage-like configuration, with the distal and proximal segments 352, 354 of the cover expanding into engagement with the wall of the vessel, but being unable to expand sufficiently to allow the distal hypotube to invert the distal segment 352 so that it may be received within the proximal section 354. In such a circumstance, the cover will not define a suitable recess for receiving the basket 320 therein.

The design shown in FIGS. 8-12 does not require that the radially expandable body 31 invert on itself to reach its fully deployed configuration. Instead, the recess 38 will always remain in place. Deployment of the body 31 distally beyond the distal tip 22 of the retrieval sheath will simply allow this recess to expand to a size wherein it may readily receive the working element of the medical device with which the cover is used.

Figure 10:
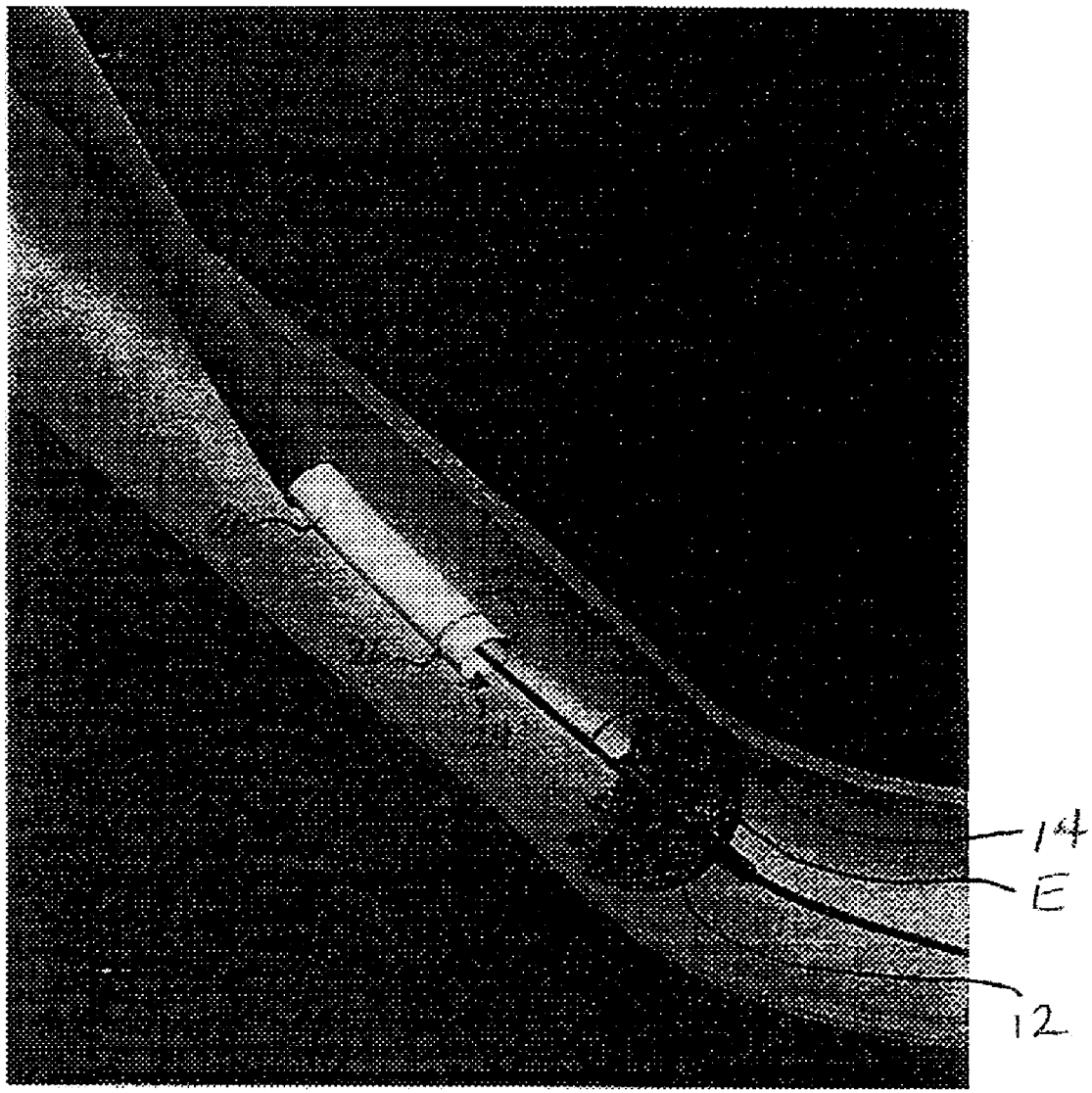
FIG. 10 is a schematic illustration showing the invention deployed within a patient's vessel and having emboli retained therein.
Figure 11:
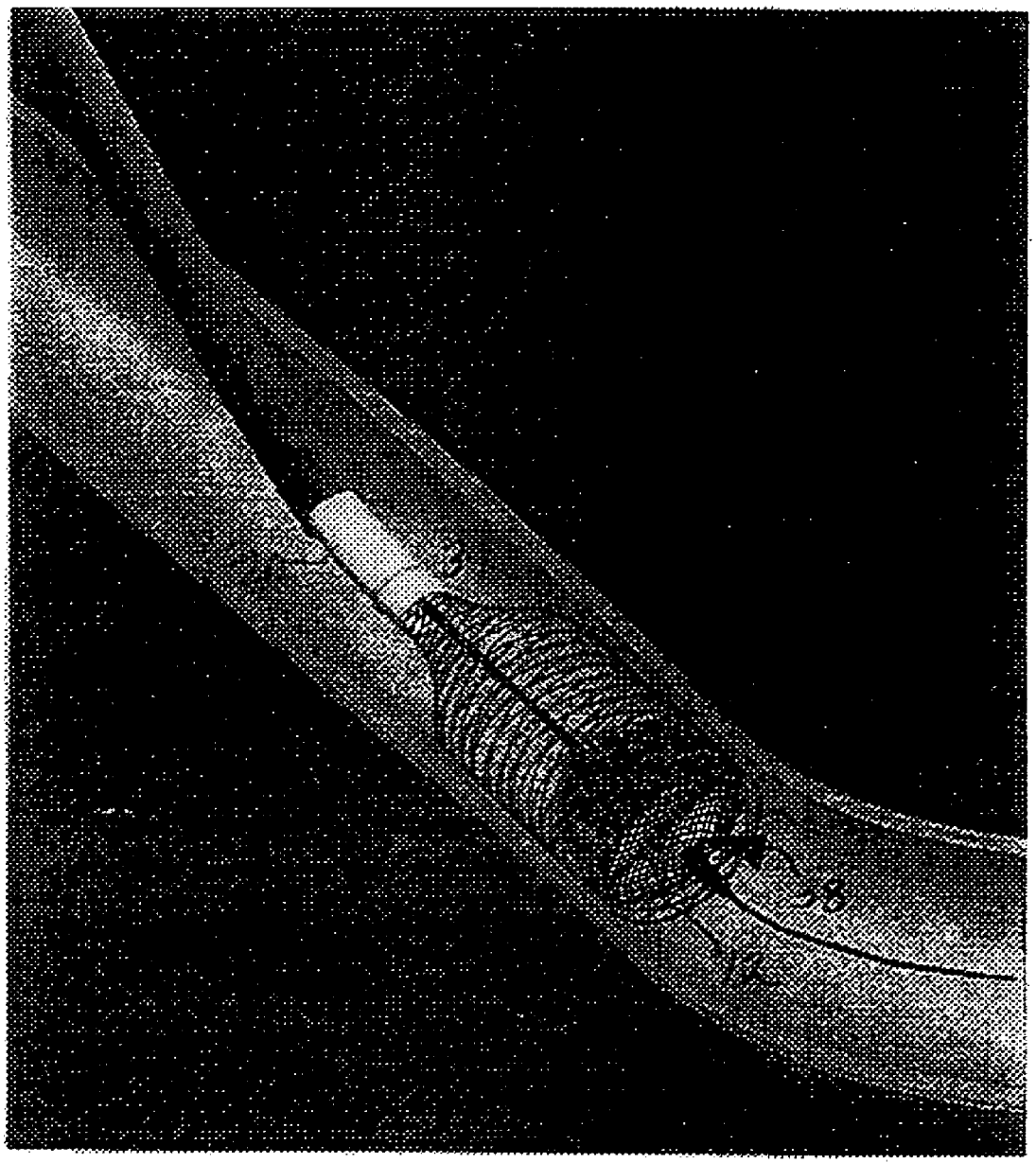
FIG. 11 is view similar to FIG. 10, but showing the trap being retracted into the confines of the cover.
Figure 12:
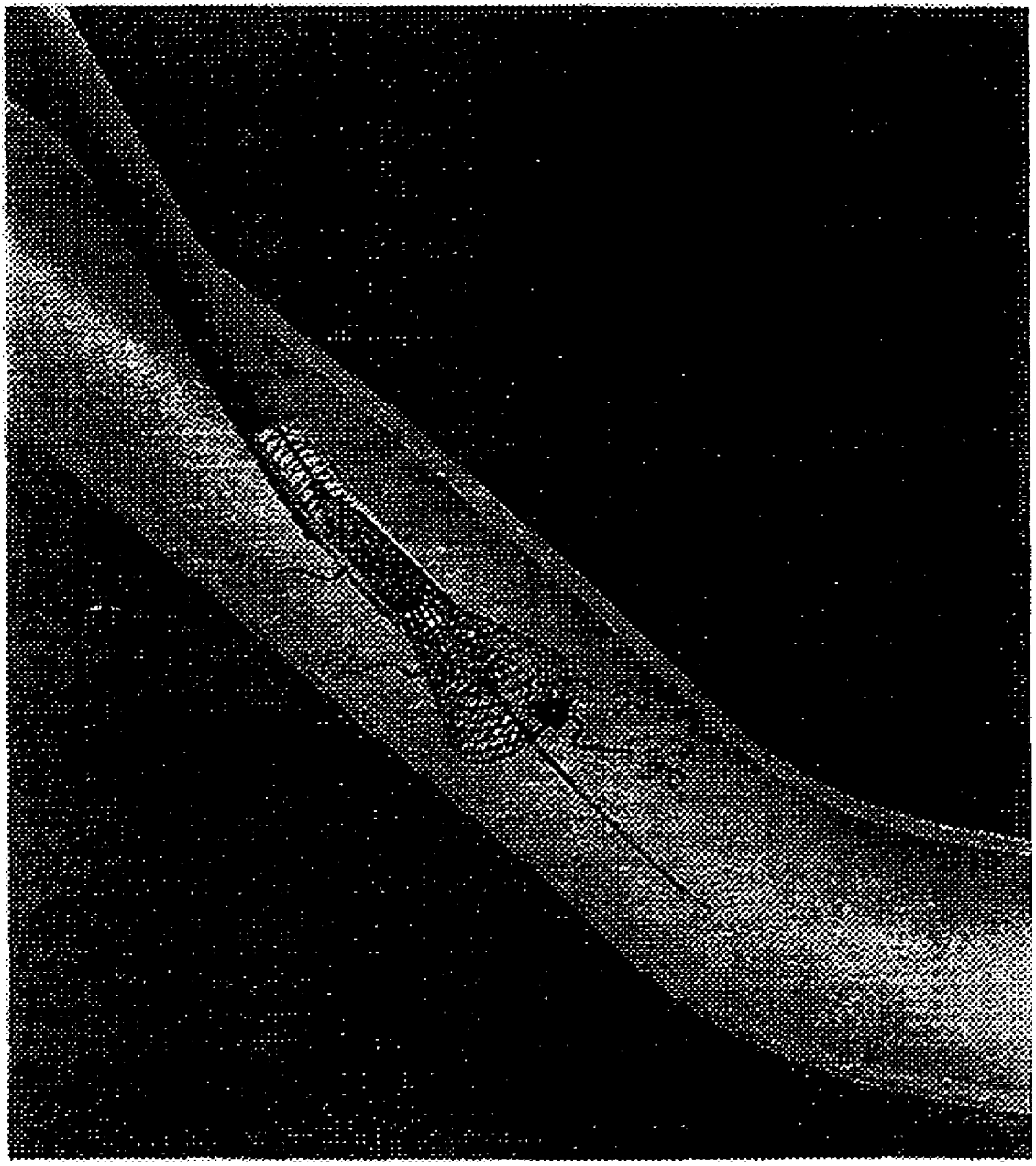
FIG. 12 is a schematic, partially cut away view of the device of FIGS. 10 and 11 showing the cover being retracted within the retrieval sheath.

While FIGS. 8 and 9 schematically illustrate the structure of the device and its various elements, FIGS. 10-12 are intended to schematically illustrate the manner in which the cover 30 may be used to retrieve a basket 12 which is full of emboli or other particular material. In FIG. 10, the deployment catheter C (discussed above in connection with FIGS. 1-5) is shown extending into the lumen of the vessel and terminating proximally of the position of the basket 12. The cavity of the basket 12 is filled with emboli E. If one were to simply pull the guidewire 12 proximally, this will tend to evert the generally umbrella-shaped basket 12, raising the possibility that the emboli E could be dumped into the bloodstream of the vessel.

In FIG. 10, the retrieval sheath 20 is positioned proximally of the basket 12, leaving a space between the distal tip 22 of the sheath 20 and the basket 12. In this Figure, the cover 30 is still within the lumen 24 of the retrieval sheath 20, much as in the configuration shown in cross section in FIG. 9.

Once the retrieval sheath, with the cover retained therein, is properly positioned, the shaft 40 of the cover 30 may be advanced distally with respect to the sheath 20. This may be accomplished either by holding the sheath 20 stationary and advancing the shaft 40 of the cover distally or by holding the shaft 40 of the cover relatively stationary and withdrawing the retrieval sheath 20 proximally to expose the readily expandable body 31 beyond the distal tip 22 of the sheath 20.

When the body 31 of the cover exits the distal end of the retrieval sheath 20, it will tend to resiliently substantially return to the configuration schematically illustrated in FIG. 8. Unlike the cover 340 of FIGS. 3-5, the body 31 of the present invention will begin to radially expand Into its final shape as soon as the distal end 36 clears the distal tip 22 of the sheath 20. Accordingly, there is no need to deploy the cover 30 so that even the proximal marker band 46 is positioned distally of the distal tip 22 of the retrieval sheath as shown in FIG. 8. Instead, the proximal portion 32 of the body 31 may remain within the lumen of the retrieval sheath 20, as suggested in FIG. 11, without compromising operation of the cover 30.

FIG. 11 illustrates the device wherein the cover has been sufficiently deployed to define a recess large enough to receive the body of the basket 12 therein. To achieve the configuration shown in FIG. 11, the shaft 14 of the vascular trap is withdrawn proximally, drawing the basket 12 within the enclosure 38.

As noted above in connection with FIG. 8, the presently preferred embodiment of such vascular trap employs a proximal band 13 which attaches a proximal end of the metal fabric defining the basket directly to the shaft of the guidewire 14 while the distal connector 15 is allowed to slide along the length of the shaft 14. Accordingly, when the operator pulls proximally on the guidewire 14, this will tend to elongate the trap and cause it to evert. In the absence of aspiration or a cover 30, this could present some difficulties.

Prior to withdrawing the shaft 14 proximally, the distal end 36 of the cover is desirably brought immediately adjacent the basket 12. In a preferred embodiment, the distal end 36 of the body 31 of the cover defines a distal opening having a maximum dimension which is at least as great as the maximum dimension of the proximal profile of the basket 12, i.e., the maximum dimension of the proximal projection of the deployed basket. If the vessel is large enough, this would permit the cover to simply slide around the basket 12 without significantly stressing the basket and causing it to collapse in any way. More likely than not, though, there will be insufficient clearance between the basket 12 and the wall of the vessel to permit the cover to readily slide between the vessel and the basket. Accordingly, the distal end of the cover will typically be brought into engagement with a surface of the basket 12. This will form between the cover and the basket and enclosure that includes both the cavity of the basket and the recess 38 of the cover. This movement of the cover distally into engagement with the medical device may be achieved either by actually physically moving the cover distally in an absolute sense, or simply withdrawing the basket 12 toward the cover which will effectively move the cover distally with respect to the medical device.

FIG. 11 illustrates the relative positions of the elements of the invention if the operator continues to withdraw the guidewire 14 proximally after the cover initially engages the surface of the basket 12. The basket has started to evert into a more oblong shape rather than the umbrella-shape shown in FIG. 10. Nonetheless, the emboli still are retained within the enclosure defined by the cover and the basket.

In one preferred embodiment, the body 31 of the cover is at least as long as the working element of the medical device which is to be retrieved therewith. This permits the working element to be entirely enclosed by the cover during the retrieval process, enhancing the likelihood of a successful retrieval without inadvertent dumping of the matter captured by the medical device back into the patient's body. While the cover can be little longer than the working element of the medical device, it is anticipated that the cover may be significantly longer than that working element. This will permit an operator greater flexibility in using the device without adding unduly to the cost.

FIG. 12 schematically illustrates the next stage of the method of removing the medical device from the patient's vascular system. In this view, the retrieval sheath has been moved distally with respect to the cover. As suggested above, this may be achieve either by moving the retrieval sheath distally along the cover or by withdrawing the cover (and, optimally, the medical device) proximally while holding the retrieval sheath 20 stationary. Urging the retrieval sheath distally with respect to the cover urges the cover to collapse about the medical device received therein. This causes the cover to tightly engage the surface of the medical device, helping better encase any particular matter received within the enclosure and limit the likelihood that it may spill back into the patients vascular system. It also presents the device with a radially reduced profile, making it easier to withdraw the device from the patients body without undue trauma.

Looking at the device in FIG. 12, the system has a particular configuration which Is unique to the present invention. In this configuration, the working element of the medical device is completely retained within the recess 38 of the body 31 of the cover such that the distal end 36 of the cover 30 is positioned distally beyond the distal end of the working element 12. In FIG. 12, at least a proximal length of the basket 12 and the body 31 of the cover are retained within the lumen of the retrieval sheath 20. This retrieval sheath radially compresses the proximal length of the cover such that an intermediate portion of the generally tubular wall 34 of the body 31 tightly engages a surface of the basket 12.

If so desired, the cover 30 and basket 12 may be further retracted so that they are both completely enclosed within the lumen of the retrieval sheath 20 prior to withdrawing the device from the patient's vessel. This is not necessary for effective operation of the current device, though, and may be left up to the physician's choice during the procedure. It should also be noted that the configuration shown In FIG. 12 may be further collapsed by withdrawing the basket 12, cover 30 and retrieval sheath 20 proximally into the deployment catheter C, thereby further encasing the emboli and making it easier to withdraw the device from the vascular system.

Figure 7:
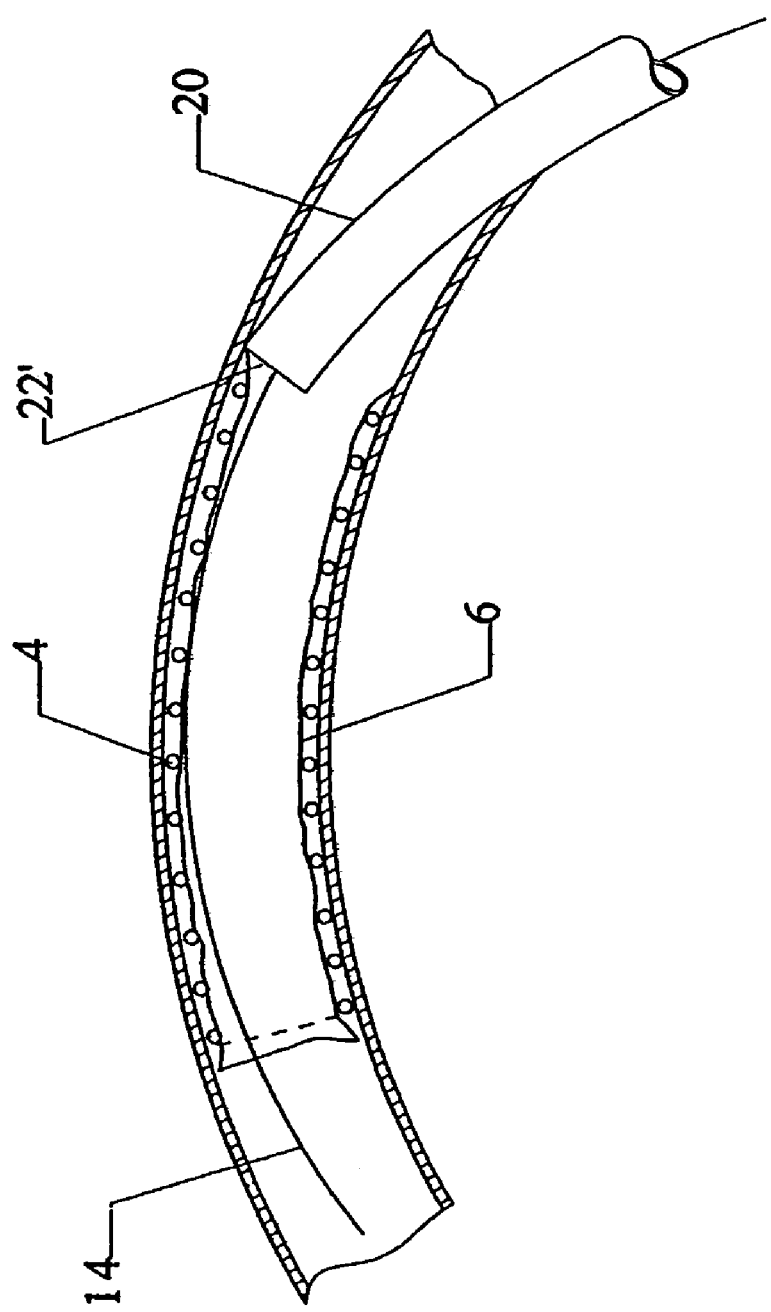
FIG. 7 is a schematic illustration of a retrieval sheath catching on a vascular obstruction proximally of the desired distal deployment site.

FIG. 7 illustrates one problem which could be encountered in deploying a medical device retrieval system 10 of the invention across a vascular obstruction. The vascular obstruction in FIG. 7 is typified as a stent 4 having a stenotic lesion 6 partially occluding the lumen thereof, but this is selected merely for illustration. Much the same problem could also be encountered with a variety of other vascular obstructions.

The illustrated deployment sheath 20 has a blunt distal tip 22'. Due to the curvature of the vessel where the stent is located, the retrieval sheath tends to drift upwardly toward the outside of the curve rather than easily tracking the shaft 14 of the medical device through the center of the vessel. This problem becomes even more pronounced if the retrieval sheath is made stiffer, such as by incorporating metallic braid into the wall of the sheath, to improve pushability. In some instances, it can take undue time and effort to manipulate the distal tip of the retrieval sheath to clear the obstruction. In addition, use of excess force or movement of the sheath to clear the obstruction risks displacing the working element (not shown) of the medical device from the treatment site where it has been deployed.

Figure 13:
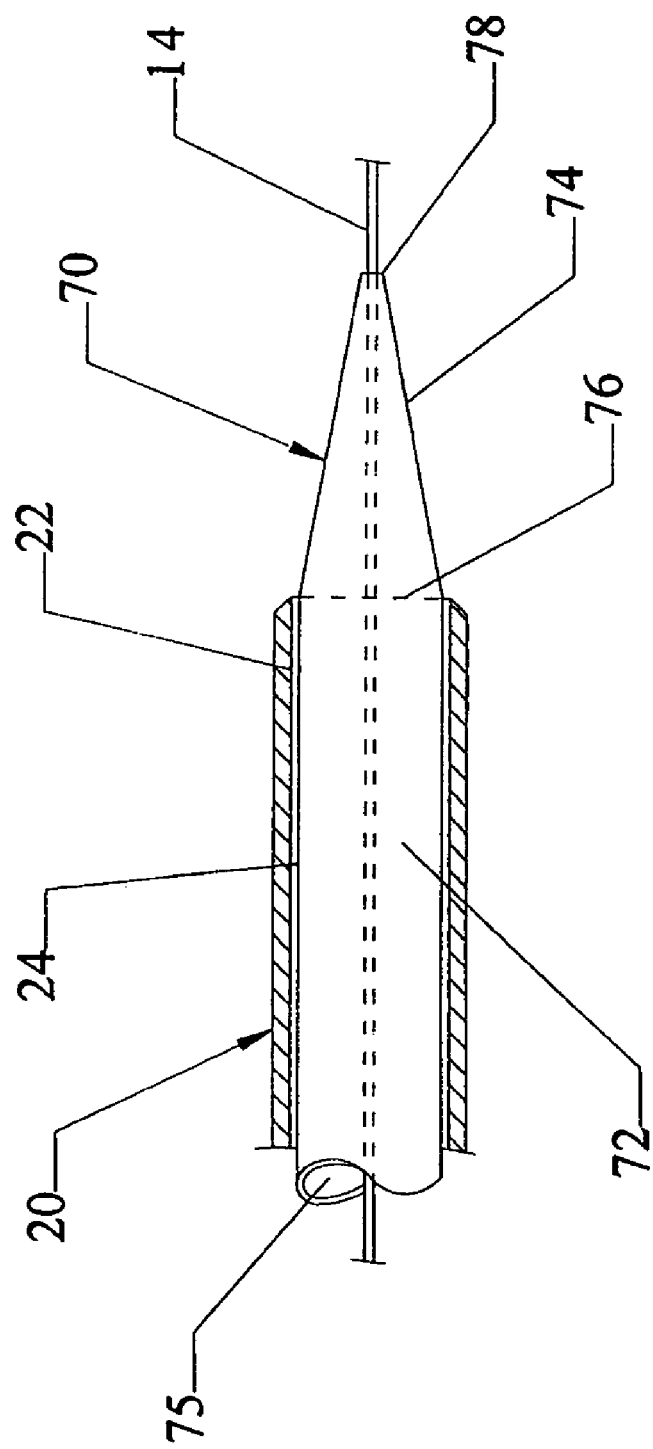
FIG. 13 is a schematic partial cross sectional view of a distal portion of a medical device retrieval system of the invention utilizing a deployment stylet.
Figure 14:
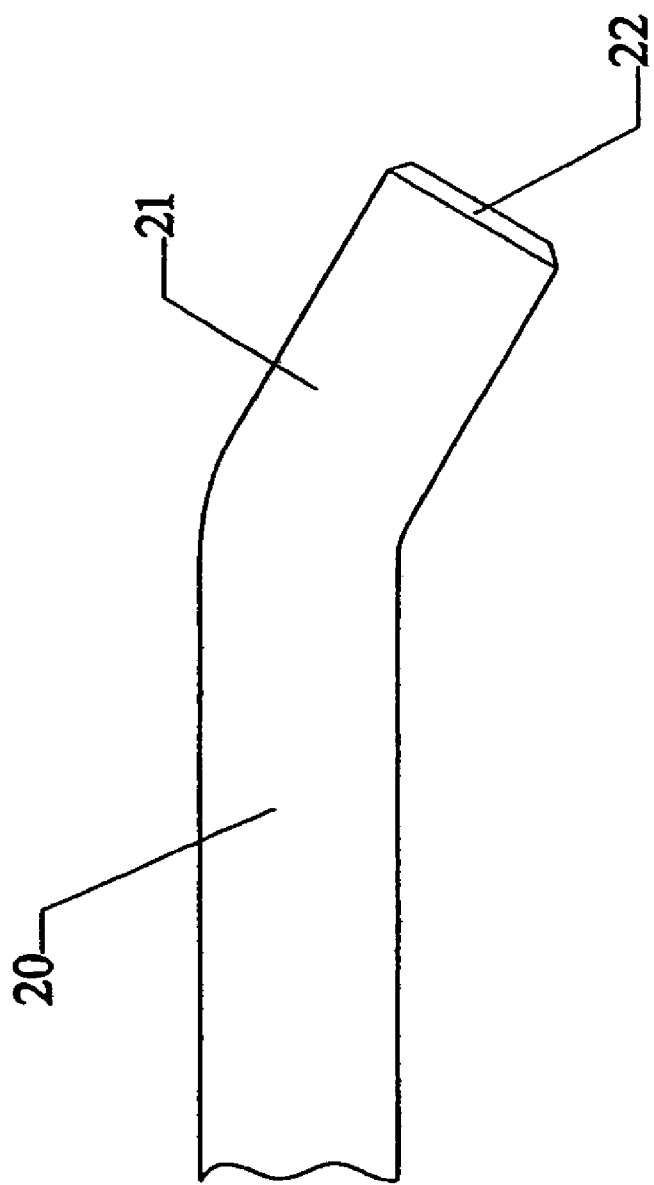
FIG. 14 is a schematic side view of a distal length of an alternative retrieval sheath for use with the invention.

FIGS. 13 and 14 illustrate two proposed solutions to ameliorate these deployment difficulties. A first solution is illustrated in FIG. 13 while FIG. 14 illustrates another improvement which may be used alone or in conjunction with the device of FIG. 13.

Turning first to FIG. 13, the retrieval sheath 20 shown therein includes a deployment stylet 70 slidably received in the lumen 24 thereof. This stylet has a lumen 75 within which the shaft 14 of the medical device is received, permitting the stylet to slide along that shaft 15 with the retrieval sheath 20. The stylet 70 is provided with an elongate tubular body 72 and a tapering distal tip 74. In use, the body 72 of the stylet desirably extends along the entire length of the retrieval sheath so that the proximal end of the stylet (not shown) extends proximally beyond the proximal end of the retrieval sheath so an operator may selectively control the stylet independently of the guide wire and of the retrieval sheath.

The distal tip 74 of the stylet tapers from its proximal end 76 to its distal end 78. At its proximal end, the distal tip has an outer diameter which approximates the diameter of the lumen 24 of the retrieval sheath at the distal end 22 thereof. As illustrated, it is not intended that the stylet 70 completely fill the lumen 24 of the sheath as that would lead to undue friction in moving the stylet relative to the sheath. The outer diameter of the sheath at the proximal end 76 of the tip 74 need only be dose enough to the diameter of the distal lumen of the sheath 20 to avoid a sharp, traumatic change in diameter which would be likely to catch on vascular obstructions and hinder deployment of the sheath 20 in the vessel. The transition from the distal tip 74 of the stylet to the outer diameter of the sheath 20 can be further eased by providing the distal tip 22 of the sheath 20 with a beveled distal end.

The distal end 78 of the stylet's distal tip 74 has an outer diameter which more closely approximates the outer diameter of the medical device shaft 14. It is not expected that this distal end 78 be infinitely thin and track directly against the surface of the shaft 14. Again, it is sufficient that the distal end 78 of the stylet be close enough to the diameter of the shaft 14 of the medical device to avoid a sharp, traumatic change in diameter which would be likely to catch on vascular obstructions and hinder deployment of the sheath 20 in the vessel.

When the stylet is deployed such that its distal tip 74 extends distally beyond the distal tip 22 of the retrieval sheath, the stylet provides a transition between the shaft 14 of the medical device and the distal end of the retrieval sheath 20. This makes it easier to track the shaft 14 and guide the device into position across a vascular obstruction. FIG. 13 illustrates the stylet positioned such that the proximal end 76 of the distal tip 74 is positioned immediately adjacent the distal tip 22 of the retrieval sheath, but this is not necessary. If the body 72 of the stylet has a substantially constant diameter over the relevant length, the stylet can be moved distally relative to the sheath 20 such that the body extends beyond the distal end of the sheath. This will not cause any undue problem as the outer diameter of the body is desirably substantially the same as the outer diameter of the proximal end 76 of the distal tip.

Use of the retrieval sheath 20 with the stylet 70 can be varied. If so desired, one can use the stylet in each and every deployment of the retrieval system of the invention. However, as outlined below, use of the stylet adds an additional step to the retrieval process and its use may be reserved for those circumstances where the operator either expects to encounter a vascular obstruction or has already encountered such an obstruction.

In use, the stylet 70 and the cover 30 are exchangeable for one another, i.e., either the stylet or the cover may track along the shaft 14 within the lumen 24 of the retrieval sheath, but both cannot be used at the same time. Instead, one must be removed and replaced with the other. If the operator anticipates a vascular obstruction (or he or she wants to avoid exchanging devices twice if an obstruction is encountered), he or she can initially deploy the sheath 20 with the stylet. This may be accomplished by positioning the stylet 70 with respect to the sheath 20 such that the distal tip 74 of the stylet extends distally beyond the distal tip 22 of the sheath. Optimally, both the stylet and the sheath are advanced together along the shaft 14 until the distal tip 22 of the sheath is in a desired position with respect to the working element of the medical device. (In most circumstances, this will be at a location wherein the distal tip of the sheath is near the working element, but spaced proximally therefrom, as discused above in connection with FIG. 11.).

Once the sheath is in position, the stylet 70 may be exchanged for the cover 30. This may be done in much the same fashion that catheters are exchanged in a typical balloon angioplasty procedure or the like. In most circumstances, an exchange wire will be attached to the proximal end of the shaft 14 of the medical device and the stylet 70 can be retracted proximally onto the exchange wire. Thereafter, the exchange wire can be disconnected and the cover may be advanced along the shaft 14 through the lumen 24 of the retrieval sheath. Using the marker band 26 of the retrieval sheath and the marker band 13 of the basket 12 (for example), any final adjustments to the position of the sheath with respect to the working element of the medical device can be made prior to deployment of the cover.

The cover 30 may then be moved distally with respect to the sheath 20, either by distally advancing the cover or proximally retracting the sheath. As noted above, this permits the body 31 of the cover to radially expand into a deployed configuration wherein the distal end remains distally open and the enclosure is radially expanded. The cover may then be moved distally with respect to the working element of the medical device and into engagement with a surface of the medical device to form therebetween an enclosure. Optimally (but not necessarily, depending on the configuration of the medical device and the shape of the cover), the cover is advanced further with respect to the working element until the entire working element is effectively received in the recess 38 of the cover. Thereafter, the retrieval sheath is moved distally with respect to the cover to urge the cover to collapse about the working element and tightly engage the surface of the working element to retain any debris in the enclosure.

FIG. 14 illustrates another improvement of the sheath 20 of the invention. In this embodiment, a distal length 21 of the sheath 20 is bent at an angle with respect to the body of the sheath. If a vascular obstruction is encountered, this distal bend will permit the operator to clear the obstruction by reorienting the sheath so that the distal tip 22 thereof is spaced toward the center of the vessel and away from the obstruction, whereupon the sheath can be further advanced. An angle of between about 5 and about 30° is believed to be sufficient for most purposes without unduly interfering with the proper deployment and retrieval of the cover 30. The length of the distal length 21 can be varied as needed. In most circumstances, it is envisioned that the distal length 21 will be 5 cm or less, with a length of 1 cm to 3 cm being most likely. As noted previously, the sheath 20 of FIG. 14 with its bent distal length 21 may be used instead of or in conjunction with the stylet 70 shown in FIG. 13.

While a preferred embodiment of the present invention has been described, it should be understood that various changes, adaptations and modifications may be made therein without departing from the spirit of the invention and the scope of the appended claims.

What is claimed is:

1. A medical device retrieval system, comprising:
   a) a medical device comprising a vascular filter carried by a flexible, elongate shaft, the vascular filter having a proximal profile, the shaft extending proximally from the vascular filter; and
   b) a retrieval sheath slidably carried along the shaft of the medical device, the retrieval sheath having a body and a distal tip comprising a distal length of the retrieval sheath, the body having a first longitudinal axis, the distal tip having a second longitudinal axis, the distal length being no greater than 5 cm, the distal tip being bent at an angle of between about 5° and about 30° with respect to the body such that the second longitudinal axis is bent with respect to the first longitudinal axis at an angle of between about 5° and about 30°.

2. The system of claim 1 wherein the distal length is between about 1 cm and about 5 cm in length.

3. The system of claim 1 wherein the distal tip further comprises a radiopaque marker band.

4. A retractable medical device system, comprising:
   a) a medical device comprising a vascular filter carried by a flexible, elongate shaft; and
   b) a retrieval sheath, the retrieval sheath having a lumen and being slidable with respect to the medical device, at least a proximal length of the vascular filter of the medical device being retained within the lumen of the retrieval sheath when the medical device is retracted, the retrieval sheath having a body and a distal tip comprising a distal length of the retrieval sheath, the body having a first longitudinal axis, the distal tip having a second longitudinal axis, the distal length being no greater than 5 cm, the distal tip being bent at an angle of between about 5° and about 30° with respect to the body such that the second longitudinal axis is bent with respect to the first longitudinal axis at an angle of between about 5° and about 30°.

5. A system according to claim 4, wherein the distal tip is bent at an angle of about 5° with respect to the body.

6. A system according to claim 4, wherein the distal tip is bent at an angle of about 30° with respect to the body.

7. A method of retrieving particulate or other foreign material within a channel of a patient's body, comprising:
   a) providing a medical device having a vascular filter and a flexible, elongate shaft adapted to follow a path within the channel; and a retrieval sheath moveable with respect to the shaft, the retrieval sheath having a body and a distal tip comprising a distal length of the retrieval sheath, the body having a first longitudinal axis, the distal tip having a second longitudinal axis, the distal length being no greater than 5 cm, the distal tip being bent at an angle of between about 5° and about 30° with respect to the body such that the second longitudinal axis is bent with respect to the first longitudinal axis at an angle of between about 5° and about 30°;
   b) positioning the medical device within the channel;
   c) expanding the vascular filter to engage a wall of the channel and trap the material within the channel, the retrieval sheath being spaced proximally of the vascular filter along the shaft of the medical device; and
   d) withdrawing the medical device proximally so that at least a proximal length of the vascular filter of the medical device is retained within a lumen of the retrieval sheath.

8. A method according to claim 7, wherein the distal tip is bent at an angle of about 5° with respect to the body.

9. A method according to claim 7, wherein the distal tip is bent at an angle of about 30° with respect to the body.

10. A method according to claim 7, wherein the sheath has a lumen large enough to contain the vascular filter.

11. A method according to claim 8, wherein the sheath has a lumen large enough to contain the vascular filter.

12. A method according to claim 7, further comprising, when a vascular obstruction of particulate or other foreign material is encountered in the positioning step, reorienting the sheath, whereupon the sheath is further advanced.

13. A method according to claim 9, wherein the sheath has a lumen large enough to contain the vascular filter.

* * * * *

UNITED STATES PATENT AND TRADEMARK OFFICE
CERTIFICATE OF CORRECTION

PATENT NO. : 7,578,830 B2  Page 1 of 1
APPLICATION NO. : 10/989787
DATED : August 25, 2009
INVENTOR(S) : Kusleika et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1317 days.

Signed and Sealed this

Seventh Day of September, 2010

David J. Kappos
*Director of the United States Patent and Trademark Office*